US007625351B2

(12) United States Patent
Messier

(10) Patent No.: US 7,625,351 B2
(45) Date of Patent: Dec. 1, 2009

(54) SYSTEM, METHOD AND APPARATUS FOR PURIFYING BIOLOGICAL FLUIDS SUCH AS BLOOD AND CONSTITUENTS THEREOF

(75) Inventor: Pierre Messier, St. Sauveur (CA)

(73) Assignee: Triosyn Holding, Inc., Williston, VT (US)

( * ) Notice: Subject to any disclaimer, the term of this patent is extended or adjusted under 35 U.S.C. 154(b) by 142 days.

(21) Appl. No.: 10/938,693

(22) Filed: Sep. 10, 2004

(65) Prior Publication Data

US 2005/0180878 A1    Aug. 18, 2005

Related U.S. Application Data

(60) Provisional application No. 60/501,780, filed on Sep. 10, 2003.

(51) Int. Cl.
  A61M 37/00      (2006.01)
  A61M 1/00       (2006.01)
  B01D 33/15      (2006.01)

(52) U.S. Cl. ............... 604/6.09; 604/6.01; 604/5.01; 604/6.03; 604/5.04; 604/5.02; 422/44; 422/48; 210/634; 210/636; 210/638; 210/645; 210/646; 210/650; 210/654; 210/660; 210/669; 210/781; 210/782; 210/800; 210/806; 210/260

(58) Field of Classification Search .......... 422/44, 422/48; 604/5.02, 5.04, 6.03, 6.01, 6.09, 604/5.01; 210/634, 636, 638, 645, 646, 650, 210/654, 660, 669, 781, 782, 800, 806, 260
See application file for complete search history.

(56) References Cited

U.S. PATENT DOCUMENTS

| 4,140,652 | A | * | 2/1979 | Korshak et al. ............ 525/54.1 |
|---|---|---|---|---|
| 4,248,736 | A | * | 2/1981 | Fuchigami et al. .......... 502/402 |
| 4,401,430 | A | * | 8/1983 | Dorson et al. ............... 604/5.04 |
| 5,240,601 | A | | 8/1993 | Mazid |
| 5,360,605 | A | | 11/1994 | Shanbrom |
| 5,370,869 | A | | 12/1994 | Shanbrom |
| 5,545,401 | A | | 8/1996 | Shanbrom |
| 5,609,864 | A | | 3/1997 | Shanbrom |
| 5,639,452 | A | | 6/1997 | Messier |
| 5,693,452 | A | * | 12/1997 | Aoai et al. ................ 430/270.1 |
| 6,045,787 | A | * | 4/2000 | Shanbrom ................ 424/78.24 |
| 6,045,820 | A | * | 4/2000 | Messier ..................... 424/443 |
| 6,096,216 | A | | 8/2000 | Shanbrom et al. |
| 6,106,773 | A | * | 8/2000 | Miekka et al. ................ 422/28 |

(Continued)

FOREIGN PATENT DOCUMENTS

WO    PCT/US2004/029398    7/2005

OTHER PUBLICATIONS

Adams GA, Swenson SD, Rock G. 1986. Survival and recovery of human platelets stored for five days in a non-plasma medium. Blood, vol. 67:3 pp. 672-675.

(Continued)

*Primary Examiner*—Tatyana Zalukaeva
*Assistant Examiner*—Ginger T Chapman
(74) *Attorney, Agent, or Firm*—Pierre J. Messier; Triosyn Holding Inc.

(57) ABSTRACT

Provided herein is an innovative hemoperfusion system and method including a thermal-fused broad-spectrum biocidal iodinated interactive polymer for the treatment of biological contaminants in body fluids. In one exemplary embodiment, the system and method utilizes a Triosyn® thermal fused broad-spectrum iodinated interactive polymer, included in a hemoperfusion column, for devitalizing high levels of cell-free microorganisms in whole blood and biological fluids in relation with the characterization of blood cells viability and function post-treatment.

9 Claims, 27 Drawing Sheets

U.S. PATENT DOCUMENTS

| | | | |
|---|---|---|---|
| 6,407,212 B1 * | 6/2002 | Morgenthaler et al. | 530/380 |
| 6,544,727 B1 * | 4/2003 | Hei | 435/2 |
| 6,736,972 B1 * | 5/2004 | Matson | 210/650 |
| 7,229,427 B2 * | 6/2007 | Mallett et al. | 604/5.04 |
| 2002/0045157 A1 * | 4/2002 | Hirai et al. | 435/2 |
| 2002/0058032 A1 * | 5/2002 | Hirai et al. | 424/140.1 |
| 2002/0197252 A1 * | 12/2002 | Brady et al. | 424/140.1 |
| 2005/0042131 A1 * | 2/2005 | Gartner | 422/45 |

OTHER PUBLICATIONS

American Association of Blood Banks, America's Blood Centers and the American Red Cross. (Aug. 2000) Circular of Information for the use of human blood and blood components pp. 1-32.

America's Blood Centers. "Bacterial Contamination of Blood Components" Jul. 2000. Online at: http://66.155.15.152/medical/bulletin_v3_n2.htm.

Amy D. Shapiro, M.D., Indiana Hemophilia and Thrombosis Center, Indianapolis, U.S.A. (1999) Platelet Function Disorders. Treatment of Hemophilia Monograph Series, No. 19. World Federation of Hemophilia: pp. 1-11.

Arthur P. Bode. (1990) Platelet Activation May Explain the Storage Lesion in Platelet Concentrates., Blood Cells (1990) vol. 16: pp. 109-126.

AuBuchon JP.; Pickard C.; Herschel L.; O'Connor JL.. Documentation of efficient leukocyte removal with a new filter. Transfusion, vol. 38:64S.

AuBuchon JP; Dodd RY. 1992. Inactivation of Microbial Contaminants of Blood Components. Clin Lab Med, vol. Dec. 12:4, pp. 787-803.

AuBuchon JP.; Elfath MD.; Popovskyk MA.; Stromberg RR.; Pickard C.; Herschel L.; Whitley P.; McNeil D.; Arnold N.; O'Connor JL.. 1997. Evaluation of a new prestorage leukoreduction filter for red blood cells. Vox Sang, vol. 72, pp. 101-106.

Buchholz DH.; AuBuchon JP.; Snyder EL.; Kandler R.; Piscitelli V.; Pickard C.; Napychank P.; Edberg S.. 1994. Effects of leukocyte reduction of the resistance of blood components to bacterial multiplication. Transfusion, vol. 34, pp. 852-857.

Wylie BR. 1993. Transfusion transmitted infection: viral and exotic diseases. Anaesth Intensive Care, vol. Feb. 21:1, pp. 24-30.

Barret BB.; Anderson.; JW.; Anderson KC.. 1993. Strategies for the avoidance of bacterial contamination of blood components. Transfusion, vol. Mar. 33:3, pp. 228-233.

Beutler, E., 1984. Determination of 2,3-Diphosphoglycerate in Erythrocytes. Red Cell Metabolism . A Manual of Biochemical Methods. 3rd ed. Orlando, Grune & Stratton, pp. 127-12.

Beaujean F, SegierJM, Le Forestier C, Duedari N. 1992. Leukocyte depletion of red cell concentrates by filtration: influence of blood product temperature. Vox Sang, vol. 62:4, pp. 242-243.

Bertolini F, Porretti L, Lauri E, Rebulla P, Sirchia G. 1993. Role of lactate in platelet storage lesion. Vox Sanguinis vol. 65 pp. 194-198.

Bertolini, F. and Murphy, S. (1994) A multicenter evaluation of reproducibility of swirling in platelet concentrates., Transfusion vol. 34, pp. 796-801.

Blajchman MA.. 1995. Bacterial contamination of blood products and the value pretransfusion testing. Immunol Invest, vol. Jan.-Feb. 24:1-2, pp. 163-170.

Blajchman MA.; Ali AM,; Richardson HL..1994. Bacterial contamination of blood components. Vox Sang, vol. 67 suppl 3, pp. 25-33.

Bove Jr..1990. Transfusion- transmitted diseases other then AIDS and hepatitis. Yale J Biol Med, vol. Sep.-Oct. 63:5, pp. 347-351.

Weber, David J., Barbee, Susan L., Sobsey, Mark D. and Rutala, William A. 1999. The Effect of Blood on the Antiviral Activity of Sodium Hypochlorite, a Phenolic, and a Quaternary Ammonium Compound. Infection Control and Hospital Epidemiology, vol. 20, pp. 821-827.

Wallas, C.H.; 1979. Sodium and Potassium Changes in Blood Bank Stored Human Erythrocytes. Transfusion, 19(2), pp. 210-215.

Busch MP; Lee T.. 1995. Role of Donor Leukocytes and Leukodepletion in transfusion-Associated Viral Infections. Clinical Benefits of Leukodepleted Blood Products. edited by Joseph Sweeney, M.D. and Andrew Heaton, M.D.,R.G. Landes Company, chapter 8, pp. 99-112.

Cabantchik, Z.I., Silfen J., Firestone R.A., Krugliak M., Nissani E. and Ginsburg H., 1989. Effects of Lysosomotropic Detergents on the Human Malarial Parasite Plasmodium Falciparum in In Vitro Culture. Biochemical Pharmacology, vol. 38, No. 8, pp. 1271-1277.

Wagner SJ.; Friedman LI.; Dodd RY.. 1994. Transfusion-associated bacterial sepsis. Clin Microbiol Rev, vol. Jul. 7:3, pp. 290-302.

Van der Meer PF, Pietersz RN, Nelis JT, Hinloopen B, Dekker WJ, Reesink HW, 1999. Six filters for the removal of white cells from red cell concentrates, evaluated at 4 degrees.

Chu RW. 1999. Leukocytes in Blood Transfusion: Adverse effects and their prevention. HKMJ, vol. 5, No. 3, pp. 280-284.

Coleman, Roger; Holdsworth, George. 1975. Effects of Detergents on Erythrocyte Membranes: Different Patterns of Solubilization of the Membrane Proteins by Dihydroxy and Trihydroxy Bile Salts. Biochemical Society Transactions, vol. 3, pp. 747-748.

Corash, Laurence, 1999. Inactivation of Viruses, Bacteria, Protozoa, and Leukocytes in Platelets Concentrates: Current Research Perspectives, Transfusion Medicine Reviews, vol. 13:1, pp. 18-30.

Dodd RY. 1998. Transmission of Parasites by Blood Transfusion. Vox Sang, vol. 74, suppl. 2, pp. 161-163.

Dodd RY. 1992. The risk of transfusion-transmitted infection. New England Journal of Medicine, vol. Aug. 6 327:6, pp. 419-421.

Dodd, RY., 1990. Will Blood Products Be Free of Infectious Agents? : Transfusion Medicine in the 1990's. In Nance SJ ed. Arlington, VA, American Association of Blood Banks, pp. 223-251.

Fratantoni, J.C., Poindexter, B.J., and Bonner, R.F. (1984) Quantitative assessment of platelet morphology by light scattering: a potential method for the evaluation of platelets for transfusion., J. Lab. Clin. Med vol. 103, pp. 620-631.

G.A. Becker, M. Tuccelli, T. Kunicki, M. K. Chalos and R. H. Aster. (1973) Studies of Platelet Concentrates Stored at 22 C and 4 C., Transfusion vol. 13, pp. 61-68.

Valeri CR, Feingold H, Marchionni LD, 1974. The relation between response to hypotonic stress and 51-Cr recovery in vivo of preserved platelets. Transfusion, vol. 14, pp. 331-337.

Girotti S., Ferri E., Cascione ML., Orlandini A., Farina L., Nucci S., Di Graci F., Budini R., 1991. Methodological Problems of Direct Bioluminescent ADP assay in Platelets and Erythrocytes. Anal. Biochem., Feb. 1, vol. 192, No. 2, pp. 350-357.

Gómez-Abonés, X.; Pinacho, A.; Ortiz, P.; Maciá, J.; Gallart, M.; Araguás, C.; Sánchez, J.M.; Teixidó. A Simple Flow-Cytometric Method For Absolute Counting of Residual White Blood Cells in Leukocyte-Reduced Packed Red Cells. Vox Sanguinis. vol. 76, pp. 64-65.

Greenwalt, TJ and Allen, CM, 1990. A Method for Counting Leukocytes in Filtered Components. Transfusion, vol. 30, No. 4, pp. 377-379.

Harmening, Denisi M., 1991. Clot Retraction, Platelet Retention/Adhesion, Platelet Aggregation, Platelet Factor 3 Availability. Clinical Hematology and Fundamentals of Hemostasis, pp. 588-592.

Valeri C.R., 1974. Oxygen Transport and Viability of Preserved Red Blood Cells. J. Med. vol. 5.

Holme S, Heaton WA. Courtright M. 1987. Improved in vivo and in vitro viability of platelet concentrates stored for seven days in a platelet additive solution. British Journal of Haematology vol. 66:2 pp. 233-238.

Holme S. 1992. Effect of additive solutions on platelet biochemistry. Blood Cells vol. 18:3 pp. 431-434.

Holme S., Moroff G., Murphy S., 1998. A multi-laboratory evaluation of in vitro platelet assays: The tests for extent of shape change and response to hypotonic shock. Transfusion, vol. 38:31, pp. 31-40.

Holmsen, H. (1994) Significance of testing platelet functions in vitro. Eur J Clin Invest. vol. 24, Suppl.1, pp. 3-8.

Illert WE.; Sänger W.; Weise W.. 1995. Bacterial contamination of single-donor blood components. Transfus Med, vol. Mar. 5:1, pp. 57-61.

James G. White ., (1992) Ultrastructural Changes in Stored Platelets., Blood Cells (1992) vol. 18: pp. 461-475.

Kekez, MM, Sattar, SA. Nov. 1997. "A new ozone-based method for virus inactivation: preliminary study." Phys Med Biology, 42 (110), pp. 2027-2039.

Kitasato Institute, Tokyo, Japan, sponsored by Yamada Corporation, 1994. Triosyn Air Technology Validation.

Valeri, C.R.; Ragno, G.; MacGregor, H.; Pivacek, L.E., 1997. The Effect of Disinfection on Viability and Function of Baboon Red Blood Cells. Photochemistry and Photobiology, 65(3), pp. 446-450.

Sweeney JD, Holme S, Stromberg RR, Heaton WA. 1995. In vitro and in vivo effects of prestorage filtration of apheresis platelets. Transfusion vol. 35:2, pp. 125-130.

Kubanek B.; Cardoso M.; Glück D.; Koerner K. 1993. Risk of infection transmission by blood components. Infusionsther Transfusionsmed, vol. Apr. 20:1-2, pp. 54-59.

Kunicki, T. J., Tucelli, M., Becker, G.A., and Aster, R.H. (1975) A study of variables affecting the quality of platelets stored at room temperature., Transfusion vol. 15, pp. 414-421.

Leach MF.; AuBuchon JP.; Pickard CA.; Herschel LH.; Cooper LK. Jenike DM.; Simpson SY.; Southworth SV.. 1998. Evaluation of glucose and Ph test strips in the detection of microbial contaminants in aphersis platelets. Vox Sanguinis, vol. 74(S1), p. 1180.

Sirchia G, rebulla P, sabbioneda L, Garcea F, Greppi N, 1996. Optimal conditions for white cell reduction in red cells by filtration at the patient's bedside. Transfusion, vol. 36, No. 4, pp. 322-327.

Ledent E, Berlin G, 1996. Factors influencing white cell removal from red cell concentrates by filtration. Transfusion, vol. 36, No. 8, pp. 714-718.

Martin C, Boisson C, Haccoun M, Thomachot L, Mege JL, 1997. Patterns of cytokine evolution (tumor necrosis factor-alpha and interleukin-6) after septic shock, hemorrhagic shock, and severe trauma. Crit care Med, vol. 25:11, pp. 1813-1819.

Sherwood WC. 1993. The significance of the blood-borne viruses: blood banking and transfusion medicine. Dev Bio Stand, vol. 81, pp. 25-33.

Murphy S, Rebulla P, Bertolini F, et al., 1994. In vitro assessment of the quality of stored platelet concentrates. Transfus Med Rev, vol. 8, pp. 29-36.

New Drug Development Institute, Tokyo, Japan, sponsored by Yamada Corporation, 1996. Triosyn Intake: Oral Irritation GLP Study.

Snyder E.; Mechanic S.; Baril L.; Davenport R. 1996. Removal of soluble biological response modifiers (compliment and chemokines) by a bedside leukoreduction filter. Transfusion, vol. 36, pp. 707.

Rebulla, Paolo and Dzik, Walter H., 1994. Multicenter Evaluation of Methods for Counting Residual White Cells in Leukocyte-Depleted Red Blood Cells. Vox Sang, vol. 66, pp. 25-32.

Rosenberg RD, Aird WC, 1999. Vascular-bed-specific hemostasis and hypercoagulable states. N Engl J Med, vol. 340, pp. 1555-1564.

Sayers MH.; Anderson KC.; Goodnough LT.; Kurtz SR.; Lane TA.; Pisciotto P.; Silberstein LE.. 1992. Reducing the risk for transfusion-transmitted cytomegalovirus infection. Ann Intern Med, vol. Jan. 1, 116:1, pp. 55-62.

Sazama K. 1994. Bacteria in blood for transfusion. A review. Arch Pathol Lad Med, vol. Apr. 118:4, pp. 350-365.

* cited by examiner

SYSTEM, METHOD AND APPARATUS FOR PURIFYING BIOLOGICAL FLUIDS SUCH AS BLOOD AND CONSTITUENTS THEREOF

CLAIM OF PRIORITY/CROSS REFERENCE OF RELATED APPLICATION(S)

This application claims the benefit of priority of U.S. Application No. 60/501,780, filed Sep. 10, 2003, which is incorporated in its entirety herein.

STATEMENT REGARDING FEDERALLY SPONSORED RESEARCH OR DEVELOPMENT

The funding for work described herein was provided by the Federal Government, under a grant from the U.S. Army Medical Research and Material Command. The Government may have certain rights in the invention.

FIELD OF THE INVENTION

This invention relates to biological fluid purification and particularly to the purification of blood and constituents thereof.

BACKGROUND OF THE INVENTION

The development of an effective purifying process active against a broad spectrum of infectious agents could improve the safety level of blood products by eliminating infectious agents that may remain undetected by current procedures or new infectious agents for which no screening test has been developed yet.

In the context of emergency conditions such as military operations on the battlefield and peacekeeping operations where supplying, conserving and testing of safe blood becomes a real challenge, the development of a technology that would provide real-time blood purification when withdrawing blood from a donor would represent an important progress.

In the context of infectious diseases, the development of a technology that would provide real-time blood purification would enable blood to be withdrawn form a patient, purified and provided back to the patient attenuating or curing the disease.

It is known that iodinated resins such as disclosed and claimed in U.S. Pat. No. 5,639,452, which issued to Pierre Jean Messier on Jun. 17, 1997 and is entitled "Iodine/resin disinfectant and a procedure for the preparation thereof" can be used to purify biological fluids such as blood. It has been found however that depending on the degree of infection and or usage of the given purification system, situations exist in which the use of such resins damage some or all of the blood constituents before effective purification is accomplished, the contact time between the resin and the cells/substrate being one of the determining factors in terms of preservation of cellular integrity.

Total length of capsule: 10.31'. Capsule inner diameter: 0.625'. Number of diffusers: 4. Triosyn type: iodine component can be 30-80% concentration range, preferably 35-50%. Volume of Triosyn: 45 g. Triosyn size: 500 microns.

Figure 22:
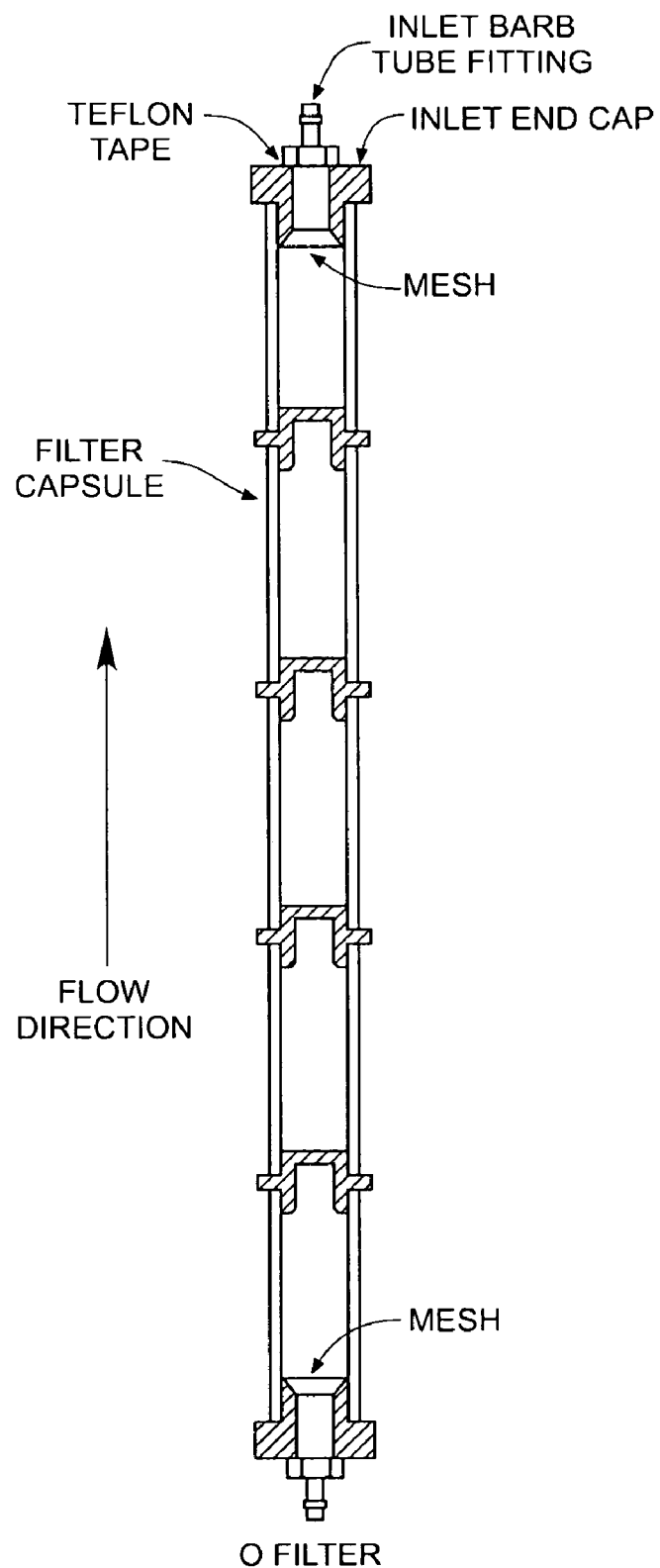

FIG. 22 depicts the characteristics of the "0" filter. Characteristics of the "0" filter: Number of capsule sections:5. Length of each capsule sections: 2.13'. Total length of capsule: 10.65'. Capsule inner diameter: 0.625'. Number of diffusers: 4. Triosyn type: iodine component can be 30-80% concentration range, preferably 35-50%. Volume of Triosyn: 45 g. Triosyn size: 500 microns.

Figure 23:
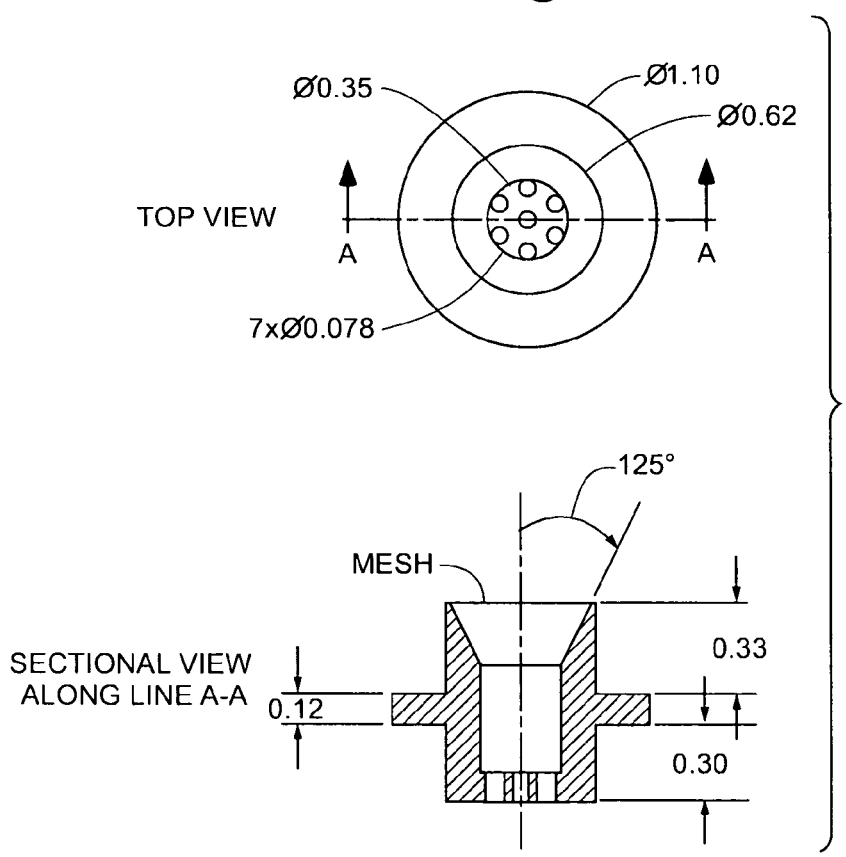

FIG. 23 depicts a top view and cross sectional view of the diffusers used within the filter units/hemoperfusion units. Note that perforated diffuser affects the flow characteristics of the blood as it passes through the unit.

Figure 24:
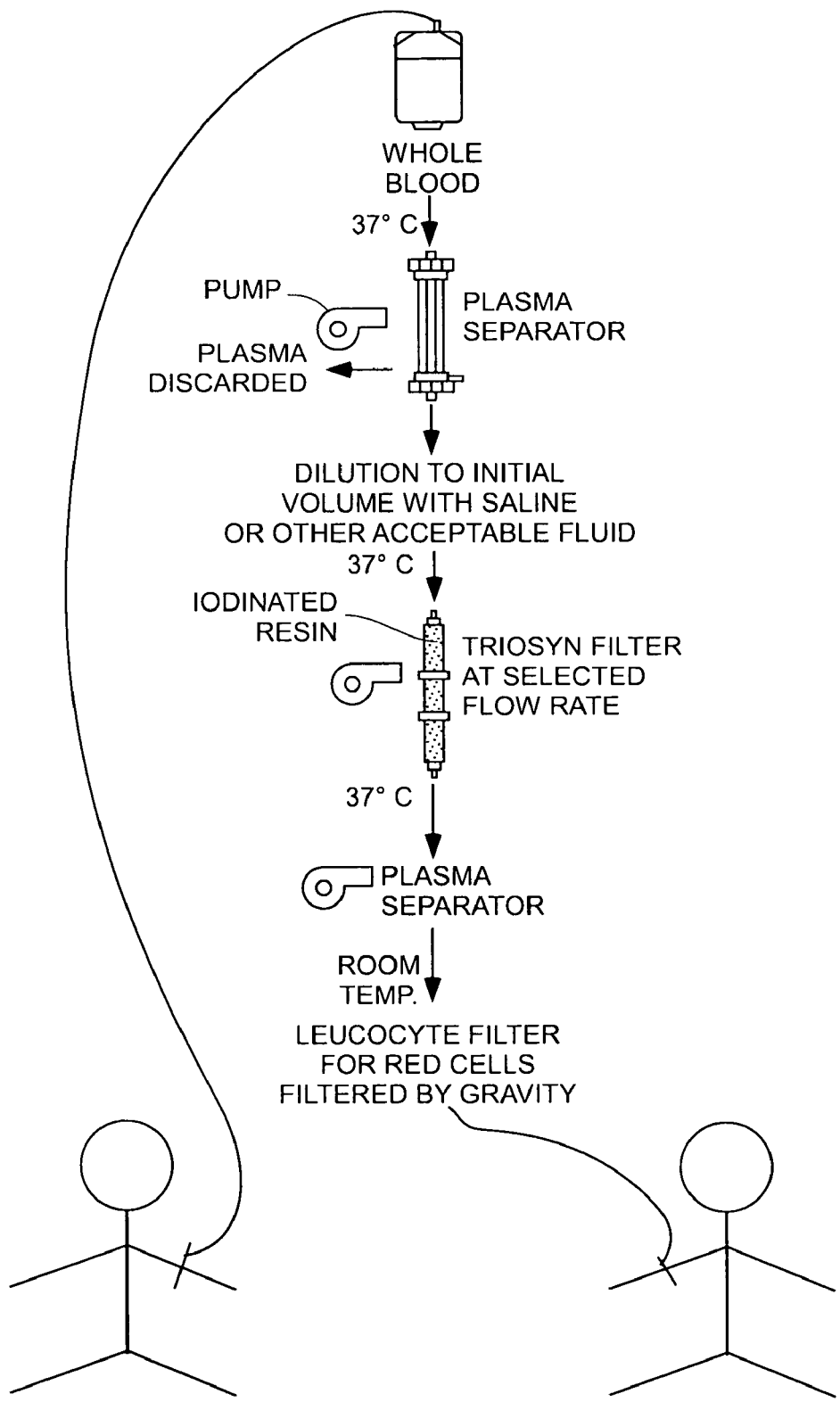

FIG. 24 depicts a battlefield transfusion scenarios using one embodiment of the Triosyn purification system.

Figure 25:
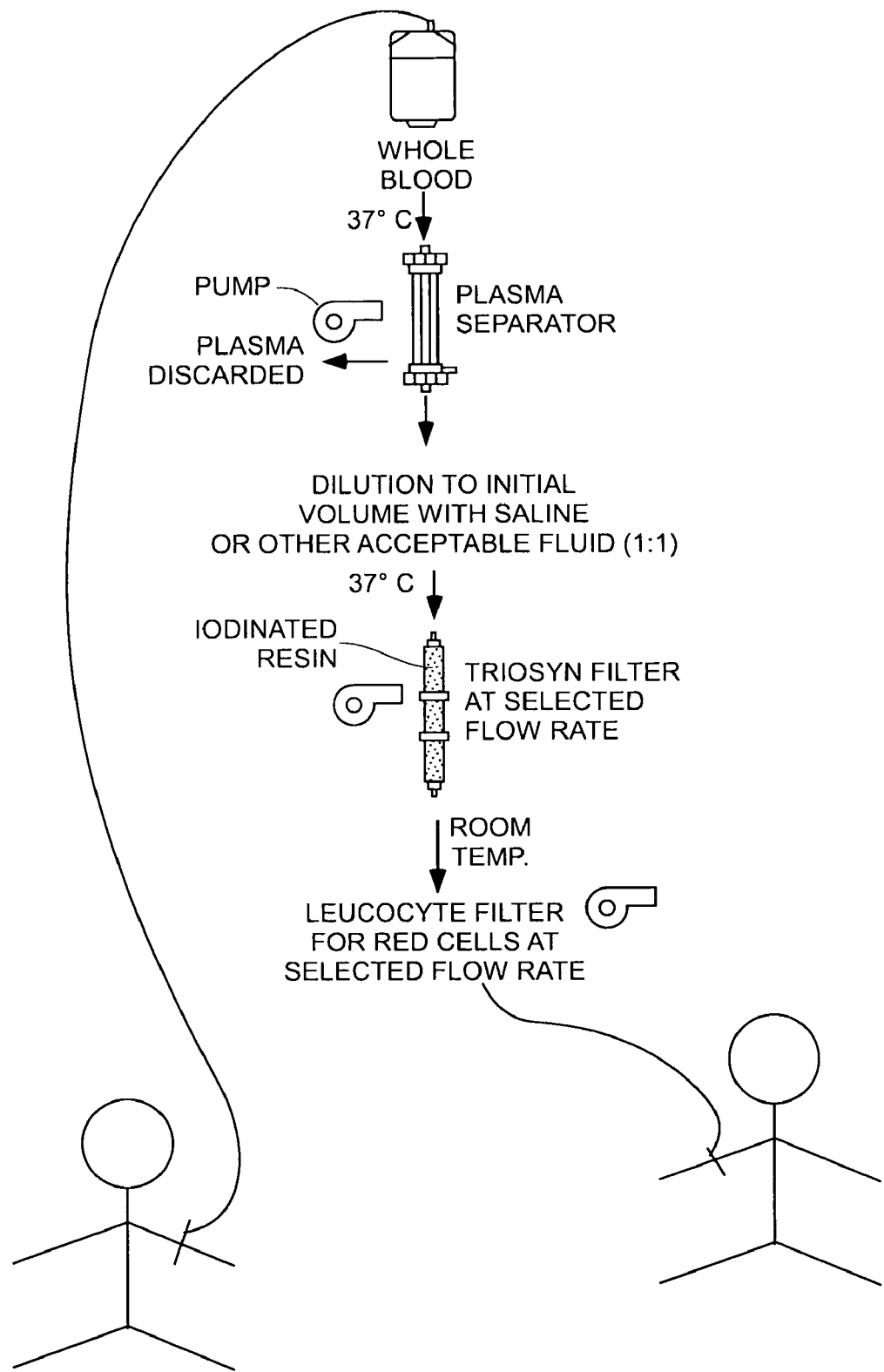

FIG. 25 depicts an alternative battlefield transfusion scenarios using an alternative embodiment of the Triosyn® Purification System.

Figure 26:
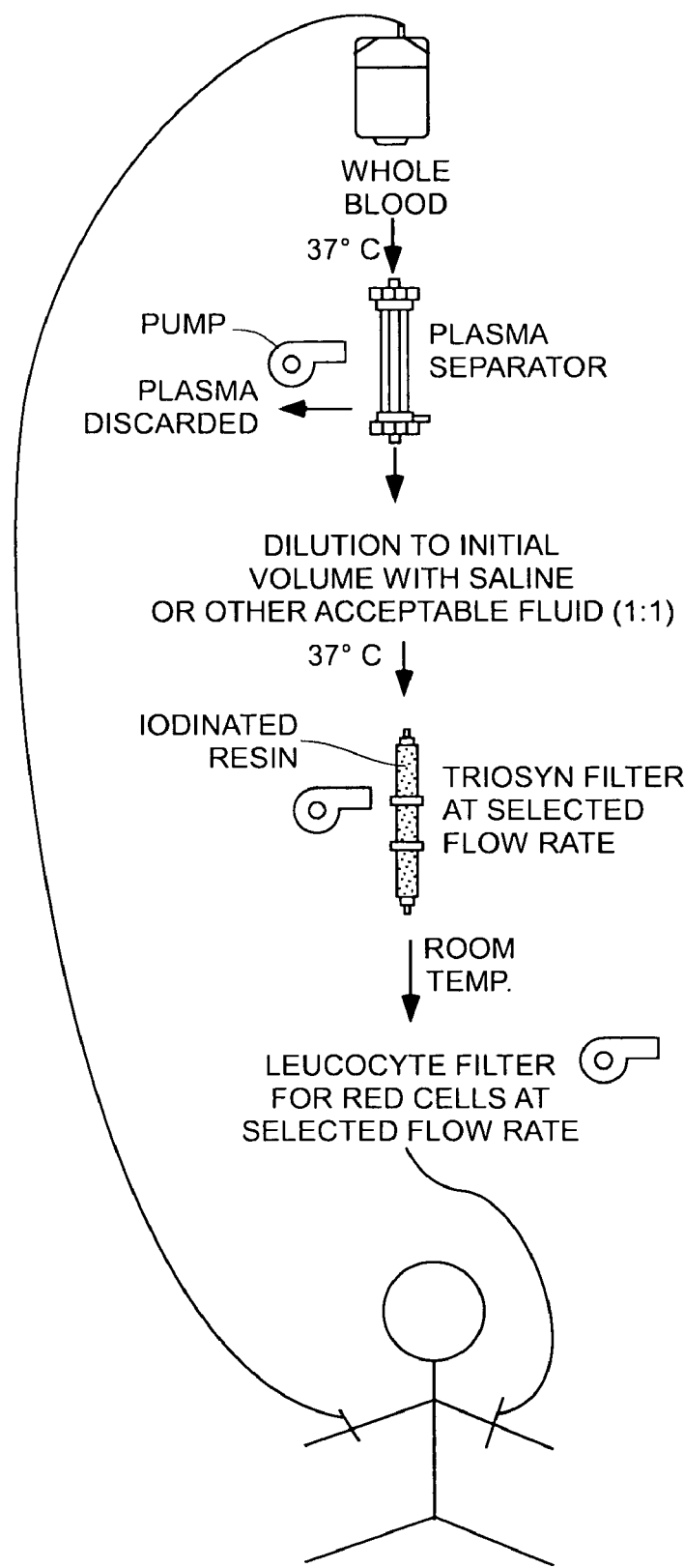

FIG. 26 depicts a process of cleansing/purifying the blood of viruses such as the SAR virus and the AIDS virus, within a human using one embodiment of the Triosyn® Purification System.

Figure 27:
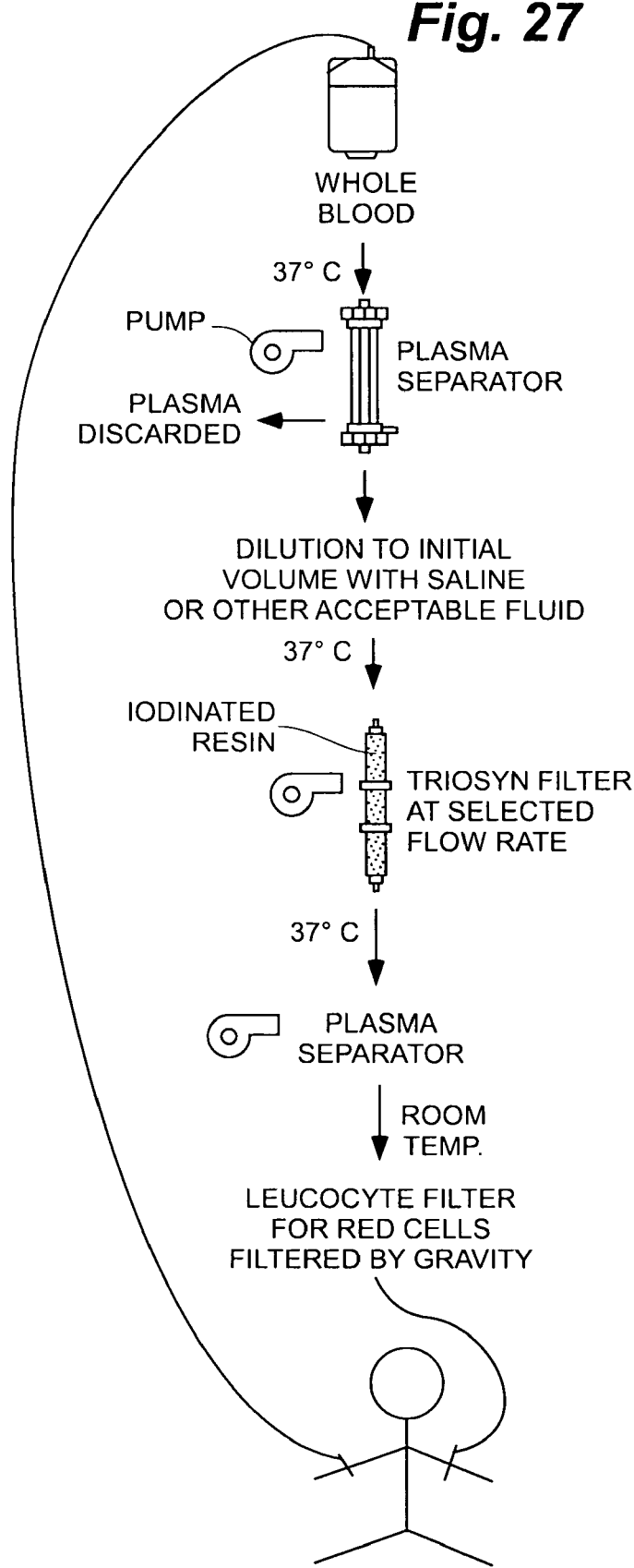

FIG. 27 depicts an alterative process of cleansing/purifying the blood of viruses such as the SAR virus and the AIDS virus, within a human using an alternative embodiment of the Triosyn® Purification System.

DETAILED DESCRIPTION OF THE INVENTION

Aspects, features and advantages of the present invention will become better understood with regard to the accompanying description with reference to the drawing figures. What follows are one or more embodiments of the present invention. It should be apparent to those skilled in the art that those embodiments provided herein are illustrative only and not limiting, having been presented by way of example only. All the features disclosed in this description may be replaced by alternative features serving the same purpose, and equivalents or similar purpose, unless expressly stated otherwise. Therefore, numerous other embodiments of the modifications thereof are contemplated as falling within the scope of the present invention as defined herein and equivalents thereto. Use of absolute terms, such as "will not," "will," "shall," "shall not," "must," and "must not," are not meant to limit the present invention as the embodiments disclosed herein are merely exemplary.

1.0 Introduction

The present invention is an innovative hemoperfusion device containing a thermal-fused broad-spectrum biocidal iodinated interactive polymer for the treatment of biological contaminants in body fluids. The development of effective decontamination processes active against a broad spectrum of infectious agents could improve the safety level of blood products by eliminating infectious agents that may remain undetected by current procedures or new infectious agents for which no screening test has been developed yet. In the context of emergency conditions, of military operations on the battlefield and peacekeeping operations, where supplying, conserving and testing of safe blood becomes a real challenge, the development of a technology that would provide real-time blood purification when withdrawing blood from a donor would represent an important progress.

2.0 Overview of Materials and Methods

The present system employs a Triosyn® thermal fused broad-spectrum iodinated interactive polymer, included in a hemoperfusion column, for devitalizing high levels of cell-free microorganisms in whole blood and biological fluids in relation with the characterization of blood cells viability and function post-treatment.

The biocidal activity of Triosyn® iodinated polymer resin involving oxidation of microbial cells, post-treatment iodide ions remaining in blood fluid were systematically quantified in order to characterize the correlation between the state of cellular integrity and the magnitude of potential residual oxidation mechanisms in the treated blood products.

It is known that the white blood cells (WBC) in blood fractions used for transfusion generally are of no therapeutic benefit to the recipient; an integrated filter for leukocytes removal was also integrated within the decontamination system.

The fundamental methodology consisted of: 1) contaminating the blood or biological fluids with high concentrations (>106 PFU or CFU/ml) of the selected microorganisms; 2) filtering the contaminated products with the Triosyn hemoperfusion unit; 3) sampling and assaying the treated specimens for presence of biological contaminants, quantification of residual iodide and characterization of the effects of the treatment on cellular integrity.

Tests were performed on bovine whole blood and blood components collected in citrate-phosphate-dextrose (CPD) anticoagulant and kept at room temperature (approximately 25° C.) until the moment of treatment.

2.1 Test Organisms

The organisms used in this procedure are MS2 coliphage (ATCC 15597-B1), *Staphylococcus aureus* (ATCC 6538) and *Escherichia coli* (ATCC 25922). The propagating host of MS2 is *Escherichia coli* (ATCC 15597). The MS2 coliphage, a bacterial virus known for its survival capabilities in the environment, is 23 nm in diameter. *Staphylococcus aureus* is a facultative anaerobic gram positive enterobacterium with a mean diameter of 0.5 to 1.5 mm. *Escherichia coli* is a facultative anaerobic gram positive vegetative bacterium presenting 1.1-1.5 mm×2.0-6.0 mm straight rods, occurring singly or in pairs. All the selected organisms show excellent resistance to environmental conditions and are hardy against chemical disinfection. They represent good models due to their non-pathogenicity, ease of preparation and assay as well as their stability in stock suspensions.

Test organisms are obtained from an outside source and used to prepare suspensions of the appropriate concentration in order to obtain high challenge concentrations of 106 PFU or CFU/ml in test matrix to be contaminated. As concerns platelet testing, platelets units were contaminated with 102 CFU of *S. aureus* in order to simulate real case scenario concentrations.

2.2 Test System (Purification Process)

The element at the source of the testing system is the Triosyn hemoperfusion unit which consists of a low-density polyethylene column including a given volume of Triosyn iodinated biocidal polymer. Throughout the evolution of the research, the first generation of prototypes was transformed to include a variable number of capsule sections as well as hydrodynamic diffusers. The volume and type of Triosyn also varied according to the various prototypes. See FIGS. 17-27.

A description of the complete integrated blood filtration process developed during this research program is found in Section 3.1. Typically, a volume of blood contaminated with challenge microorganisms was processed through the hemoperfusion prototype to be tested with the assistance of a peristaltic pump at a given flow. Samples were taken after the filtration of 300-500 ml of blood.

2.3 Controls

Positive controls comprised of CPD anti-coagulated blood, biological fluids or platelets were taken from the non-filtered portion of the original volumes. Control samples were subjected to the same storage conditions and testing procedures as the treated samples.

2.4 Flow Rate

For prototype optimization purposes, contaminated biological fluids were processed through the test system at varying flow rates ranging between 5 and 250 ml/min. The testing flow rate was controlled with the help of a Carter™ cassette pump head peristaltic system (Manostat®, Barnant Company, Illinois, USA) and validated using a stopwatch and a graduated cylinder.

Selected flow rates are specified within the result data.

2.5 Assays

2.5.1 Biocidal Efficacy

The biocidal effect of the treatment was evaluated using standard microbiology methods for MS2 phage, *S. aureus* and *E. coli* counts. Serial dilutions of the test and positive control samples were plated on MS2 specialized agar or Tryptic Soy Agar (TSA) media and incubated for appropriate period and temperature based upon the optimal growth conditions for test organism (12 h at 35.0±0.5° C. for MS2 and *E. coli;* 48 h at 35±0.5° C. for *S. aureus*) for subsequent enumeration of the number of PFU/ml or CFU/ml. The inactivation efficiency was subsequently quantified by comparing the number of CFU-PFU/ml recovered from positive controls and treated samples. For each test sample, the biocidal reduction was calculated using the following equation:

$$BR\% = \frac{C-T}{C} \times 100$$

Where:
C=Control count.
T=Count for treated sample.

2.5.2 Concentration of Residual Iodide

Residual iodide ions in blood fluid were measured for test and control samples using an iodide ion selective electrode. Ion selective electrodes (ISE) respond selectively to one species in solution. The electrode has a thin membrane separating the sample from the inside of the electrode. The internal solution contains the ion of interest at a constant activity. External solution is the biological fluid. ISE measures the potential difference across the membrane, which is dependant on the difference in activity of the iodide species between the internal solution and the biological fluid. Iodide concentration is read directly on the ion meter in millivolts and extrapolated from a calibration curve. Results are expressed in mg/L.

2.5.3 Post-treatment Effects on Cellular Integrity

Red cell and platelet viability and function were assessed using in vitro measurements as predictors of their in vivo recovery and survival rates. Hematocrit, hemoglobin, blood cells count, mean corpuscular volume (MCV), mean corpuscular hemoglobin (MCH) and mean corpuscular hemoglobin concentration (MCHC) were systematically measured using an automated blood counter (Vet ABC 45, ABX hematology, Montpellier, France).

Red blood cell potassium was identified by Valeri (71) as a good indicator of red cell injury during disinfection. Plasma samples were centrifuged and analyzed for extracellular potassium and sodium dosage using a flame photometer equipped with a fiber optic cable.

During Phase I of the study, the interpretation of the results was particularly based on the methemoglobin (MHb) parameter, because of its sensibility to oxidation. The dosage of methemoglobin using spectrophotometry techniques measures the conversion of hemoglobin in methemoglobin which shows an absorption peak at 630 nm. pH was also studied as a good indicator of the effect of the treatment on the biochemistry of the cells and the substrate.

While WBCs are not desired components of blood products for transfusion, they provide easily available data on the quality of treated blood. Consequently, the post-treatment evaluation of WBC viability was used as supplementary information on cell injury associated with disinfection during the initial down selection process of first-generation prototypes. The trypan blue exclusion dyeing method with a hemacytometer was used to evaluate the viability of white blood cells as viewed by phase microscopy.

As far as platelets are concerned, morphological score, pH, total counts and dosage of lactate and lactate dehydrogenase (LDH) enzymes were the parameters considered. As reported by Holme et Al. (1998), the results of morphological analysis were found to correlate highly with the extent of shape change (ESC) measured photometrically. In this study, Kunicki's technique for evaluating structural changes in platelets was used. The K score method is based on morphologic evaluation of platelets as viewed by phase microscopy. Platelet damage is assessed by assigning a score to individual cells showing distinct morphologic differences. The concentration of lactate and lactate dehydrogenase (LDH) enzymes in the substrate was measured using colorimetric methods read by spectrophotometry.

2.6 Leukodepletion

A method based on the literature was used for counting leukocytes in red cell products (37, 42, 62 and 77). This counting method describes a procedure for visual counting of leukocytes present in leukodepleted blood. The method uses a Nageotte counting chamber with 250 ul-grid. The sensitivity of the method is 0.1 leukocyte/ul and should be used only in products for which leukodepletion has reduced the count to levels below 5 leukocytes/ul.

3.0 Results and Discussion

3.1 Biocidal Performance

Several factors were found to improve the biocidal performance of blood constituent filters having iodinated resins therein by affecting the contact dynamics within the filters. The fluid dynamics including the velocity of the blood constituent and the residence time thereof in the filter as well as all preferential flows and pressure resistance phenomenon were found to have a direct influence on the biocidal performance of the filters. The elimination of viral particles and bacteria was significantly affected by both the viscosity and the solid content of the blood constituent. As evidenced by Table 3.1, the bacteria, which were successfully eliminated in the plasma through the iodinated resin filtration system, seem to be shielded from the disinfecting agent in the presence of erythrocytes (red blood cells).

TABLE 3.1

Effect of Substrate on *E. coli* Reduction at Constant Temperature and Flow Rate

| Filter Type | Substrate | *E. coli* Reduction | | |
|---|---|---|---|---|
| | | Avg. | Std. Dev. | n |
| O | blood | 56.78 | 24.56 | 3 |
| | plasma | 99.903 | 0.018 | 5 |
| BB | blood | 45.19 | 32.02 | 6 |
| | plasma | 99.90 | 0.14 | 2 |

This phenomenon is less evident with MS2 in which case the disinfection stage possesses a more homogeneous efficacy within the different substrates (blood, plasma or serum) (Table 3.2).

TABLE 3.2

Effect of Substrate on *S. aureus* Reduction at Constant Temperature and Flow Rate

| Filter Type | Substrate | *S. aureus* Reduction | | |
|---|---|---|---|---|
| | | Avg. | Std. Dev. | n |
| BB | blood | 80.62 | 9.37 | 6 |
| | plasma | 99.9986 | 0.0008 | 2 |

Among scientific reviews, certain phenomenon as such are reported. In fact, a few authors (Weber, Barbee, Sobsey and Rutala, 1999) observed that the presence of blood significantly reduces the antiviral activities of several chemical agents (sodium hypochlorite, a phenolic and a quaternary ammonium compound). In the light of these facts, we believe it is reasonable to hypothesize that specific affinities, due in part to differences in the composition of the membrane as well as the electric charge of the microorganisms, between certain types of blood cells or proteinic components and biological agents might be responsible for preventing adequate contact with the active ingredient and subsequent disinfection.

In order to maximize the contact efficacy created within the filtration system, several strategies were tested for different selected prototypes in order to control the parameters influencing the contact between iodinated resins and microorganisms. The set-up of hydrodynamic diffusers was first studied and optimized in order to decrease the significance of the variations in the reduction linked to the preferential flows and the fluctuations of viscosity values. It was postulated that the addition of diffusers would increase the probability of the fluid coming into contact with the iodinated resins, accomplished in two ways. First, the flow of the blood would be disrupted, causing greater dispersion of the blood over the available iodinated resins surface. Secondly, the diffusers would increase the back pressure of the blood, leading to more thorough contact with the iodinated resins beads. The results of subsequent testing suggested that the use of diffusers contributed to a better control of pressure resistance and a more homogeneous contact between the polymer and microbial entities with less variation observed in biocidal efficacy between similar prototypes.

In order to constantly work toward maximizing the efficacy of the active microorganism contact sites, the effects of pre-filtration sonication of substrate and addition of EDTA and calcium chloride ($CaCl_2$) to the substrate in order to prevent the aggregation of microorganisms were investigated. Sonication is contra-indicated for whole blood since it would induce hemolysis of erythrocytes. The obtained results did not show a significant effect of these techniques. The sonication of the filtration system was also examined, the stated hypothesis being that the micro-movements created within the filter would potentially increase the contact opportunities between the existing microorganisms and the active sites of the polymer. Moreover, the increase in temperature of the substrate as an amplification factor of the activity of the polymer was also studied. The attained results in Table 3.3 allow for observable effects of sonication and flow rate on the microbiological reduction obtained in the plasma.

TABLE 3.3A

Effects of Sonication on MS2 Reduction with Filter Prototype JJ

| Sonification Intensity | Temperature | Flow Rate | MS2 Reduction | | |
|---|---|---|---|---|---|
| % | Celcius | ml/min | Avg. % | Std. Dev. | n |
| 50% | 37 | 25 | 98.34 | 1.34 | 2 |
| | | 50 | 97.92 | — | 1 |
| 100% | 37 | 25 | 99.54 | 0.11 | 2 |
| | | 50 | 93.15 | 2.29 | 2 |
| | 42 | 25 | 99.48 | 0.05 | 2 |

Pursuant to standard operational procedure of transfusion being selective, it was decided to treat blood components separately (plasma, serum, red blood cell concentrates). In terms of separating the different blood components, a leukodepletion filter was integrated into the filtration system.

Two types of commercial filters were tried (Leukotrap.RTM., Pall Corporation, East Hills, N.Y. 11548, USA and Sepacell.RTM., Baxter Healthcare Corp, Ill., USA) in different sequences (before or after the Triosyn.RTM. unit). In parallel, different configurations were also tested in an attempt to reach the contact equilibrium sought. The optimization of working prototypes entailed the testing of numerous configurations with regards to composition and structure of the column (physical dimensions and characteristics of the column, type and amount of polymer, etc.) as well as filtration conditions (temperature, direction of flow, etc.). The integrated procedure developed for filtration of red blood cell concentrates reads as follows:

One unit (500 ml) of fresh whole blood stored at 4° C. for less than 7 days is brought to room temperature and contaminated with selected biological agent to a final concentration of $10^7$ CFU or PFU/ml. The bag is then centrifuged at 3200 RPM for 5 minutes.

With the help of a plasma extractor, the plasma is removed from the bag. 2.75 volumes of phosphate-buffered saline (PBS) are then added to the bag containing the red blood cell concentrate. The RBC concentrate is heated up to 37° C. into a thermostated waterbath.

Filtration occurs through the system at a flow of 50 ml/min. The substrate goes through the Triosyn® unit first to be recuperated in a transfer bag. The blood is allowed to cool to room temperature and is centrifuged again at 3200 RPM for 5 minutes. The PBS supernatant is removed using a plasma extractor.

Finally, the red blood cell concentrate is filtrated by gravity through a Sepacell® filter (Baxter Healthcare Corp, Il, USA) for leukocytes' removal and recuperated into an adequate bag from which samples are taken for microbiological assay, hematology and biochemistry analysis. Control samples are taken from the whole blood, after contamination; the dilution factor is accounted for in the reduction calculations.

The development of the Triosyn® integrated system allowed for a reproducible biocidal reduction rate greater than 99% against viruses and 99.9% against bacteria in presence of erythrocytes (RBC concentrates) as demonstrated in the results presented in Table 3.3. The increase obtained in terms of microbiological reduction within this system is all the more significant since it is associated with a considerable reduction of the impacts observed on cellular integrity (methemoglobin and pH levels) as discussed in section below. These results were obtained by maintaining the residual iodide levels well below the limits of the Maximum Tolerated Dose established for large blood volume transfusions.

TABLE 3.3

Biocidal Reduction for Target Microorganisms in RBC Concentrate

| | | Biochemical Parameters | | | |
|---|---|---|---|---|---|
| Microorganism | Filter Type | pH after filtration | Methemoglobin after filtration (%) | Residual Iodide mg/L | Microbiological Reduction % |
| E. coli | N-BB-767 | 7.03 | 0.00 | 221 | 99.9923 |
| | N-BB-768 | 7.17 | 0.00 | 331 | 99.9691 |
| | N-BB-769 | 7.11 | 0.96 | 286 | 99.9844 |
| | N-BB-770 | 7.08 | 1.51 | 192 | 99.9897 |
| | N-BB-771 | 7.11 | 1.18 | 216 | 99.9999 |
| S. aureus | N-BB-763 | 6.94 | 1.41 | 353 | 99.9122 |
| | N-BB-764 | 6.94 | 0.00 | 337 | 99.9744 |
| | N-BB-765 | 6.89 | 2.99 | 412 | 99.9655 |
| MS2 | N-BB-759 | 7.02 | 0.00 | 208 | 99.8062 |
| | N-BB-761 | 7.09 | 0.00 | 325 | 99.9744 |
| | N-BB-762 | 7.06 | 0.65 | 247 | 99.9654 |

Biocidal reduction objectives having been met while maintaining viable blood components, the fourth quarter activities were focused on increasing the portability and adaptability of the Triosyn® integrated system to battlefield conditions. Tests were performed with the intent of replacing the centrifugation steps by alternative blood components separation processes. This would enable the process to take place without electrical requirement or peripheral equipment other than the processing hemoperfusion system.

The first objective was to remove the centrifugation after the Triosyn® unit from the whole process while maintaining the previously obtained microbiological and biochemical results. Consequently, red blood cell concentrates were diluted in smaller PBS volumes after the first centrifugation step and the Sepacell® filtration was performed at a controlled constant flow rate.

Results obtained with *Escherichia coli* showed that the dilution level and Sepacell® flow rate were not critical for microbiological performance. Conversely, pH and residual iodide were found to be affected by dilution factors. As shown in table 3.4, tests with coliphage MS2 demonstrated that the removal of the centrifugation step affected the performance of the overall Triosyn integrated system. Moreover, biocidal performance against MS2 fell under the 99% reduction rate. For this reason, other alternatives to replace centrifugation process have been considered.

TABLE 3.4

Effect of Dilution of RBCs and Sepacell® Controlled Flow Rate on Microbiological Efficiency against MS2 Challenge for Selected Filter Prototypes

| Filter Type | Sepacell® Flow Rate | PBS Dilution Factor | n | MS2 reduction % | pH variation | Residual iodide (mg/L) |
|---|---|---|---|---|---|---|
| BB | 5 | 1:1 | 1 | 99.730 | −0.3 | 552 |
| | | 1:2 | 1 | 98.756 | −0.19 | 334 |
| | 10 | 1:0.5 | 2 | 97.922 | −0.35 | 761 |
| | | 1:2 | 2 | 85.256 | −0.18 | 114 |
| | 20 | 1:1 | 2 | 95.735 | −0.28 | 349 |
| LL | 10 | 1:0.75 | 2 | 98.537 | −0.18 | 485 |
| | | 1:1 | 6 | 96.882 | −0.23 | 504 |

In order to remove plasma from whole blood, a plasma separator, Plasmaflo® (Asahi Medical Co Ltd, Tokyo, Japan), was used. A plasma separator is a medical device used to concentrate red blood cells from whole blood by partially removing plasma. Results obtained with this filter were compared with those obtained using the centrifugal process.

TABLE 3.5

Comparative Results for Centrifugation versus Plasma Separator (Plasmaflo ®) Processes against *Escherichia Coli* and MS2 Challenges for Filter Prototypes BB at 50 Ml/Min

| Microorganism | Process | n | Methemoglobin Variation (%) | pH variation | Residual iodide (mg/L) | Microbiological Reduction (%) |
|---|---|---|---|---|---|---|
| E. coli | Centrifugation | 5 | +0.28 | −0.16 | 249 | 99.987% |
| | Plasmaflo ® | 2 | +14.34 | −0.28 | 213 | >99.9997% |
| MS2 | Centrifugation | 3 | +0.17 | −0.16 | 260 | 99.56% |
| | Plasmaflo ® | 2 | +9.04 | −0.23 | 260 | 99.10% |

As shown in table 3.5, for similar conditions, methemoglobin levels and pH seemed to be more affected when the substrate was processed through Plasmaflo® rather than being centrifuged.

The fact that more plasma remained from the Plasmaflo® process probably explains this phenomenon since it was observed that those parameters show higher values in RBC concentrates in presence of plasma. Otherwise, residual iodide remained below the Maximum Tolerated Dose limits established previously for large volume transfusions and biocidal reduction rates were maintained over 99% for viruses and 99.9% for bacteria.

Based on these findings, several tests were performed with modified filter prototypes in aim to lessen the negative biochemical effects observed with the use of a plasma separator. Those experiments led to the development of a new Triosyn® system in which two plasma filters replaced the previous centrifugation steps proposed in the previous quarter. Table 3.6 shows that up to 99.488% MS2 viral particles were efficiently eliminated from blood with biochemical parameters close to those obtained previously, suggesting minimal impacts on cellular integrity. As concerns bacterial challenge, the improved Triosyn® system proved to eliminate >99.9997% of $E.\ coli$ in RBC concentrates (please refer to table 3.5). In addition, in the light of previous observations regarding the correlation between plasma and methemoglobin levels in RBC concentrates, it is reasonable to believe that an increase in mechanical efficiency of the plasma separation process would lead to even lower methemoglobin levels.

TABLE 3.6

Biocidal Performance of Triosyn ® Integrated System against MS2 Challenge when Replacing Centrifugation Processes by Two Plasma Filters

| Filter prototype | Methemoglobin Variation (%) | pH Variation | Residual iodide (mg/L) | MS2 Reduction (%) |
|---|---|---|---|---|
| N-LL-835 | +4.83 | −0.24 | 400 | 99.488 |
| N-LL-836 | +7.17 | −0.18 | 414 | 98.815 |
| N-LL-837 | +5.24 | −0.19 | 255 | 98.794 |
| N-LL-838 | +8.02 | −0.22 | 482 | 99.388 |
| Average | +6.32 | −0.21 | 388 | 99.121 |

Figure 1:
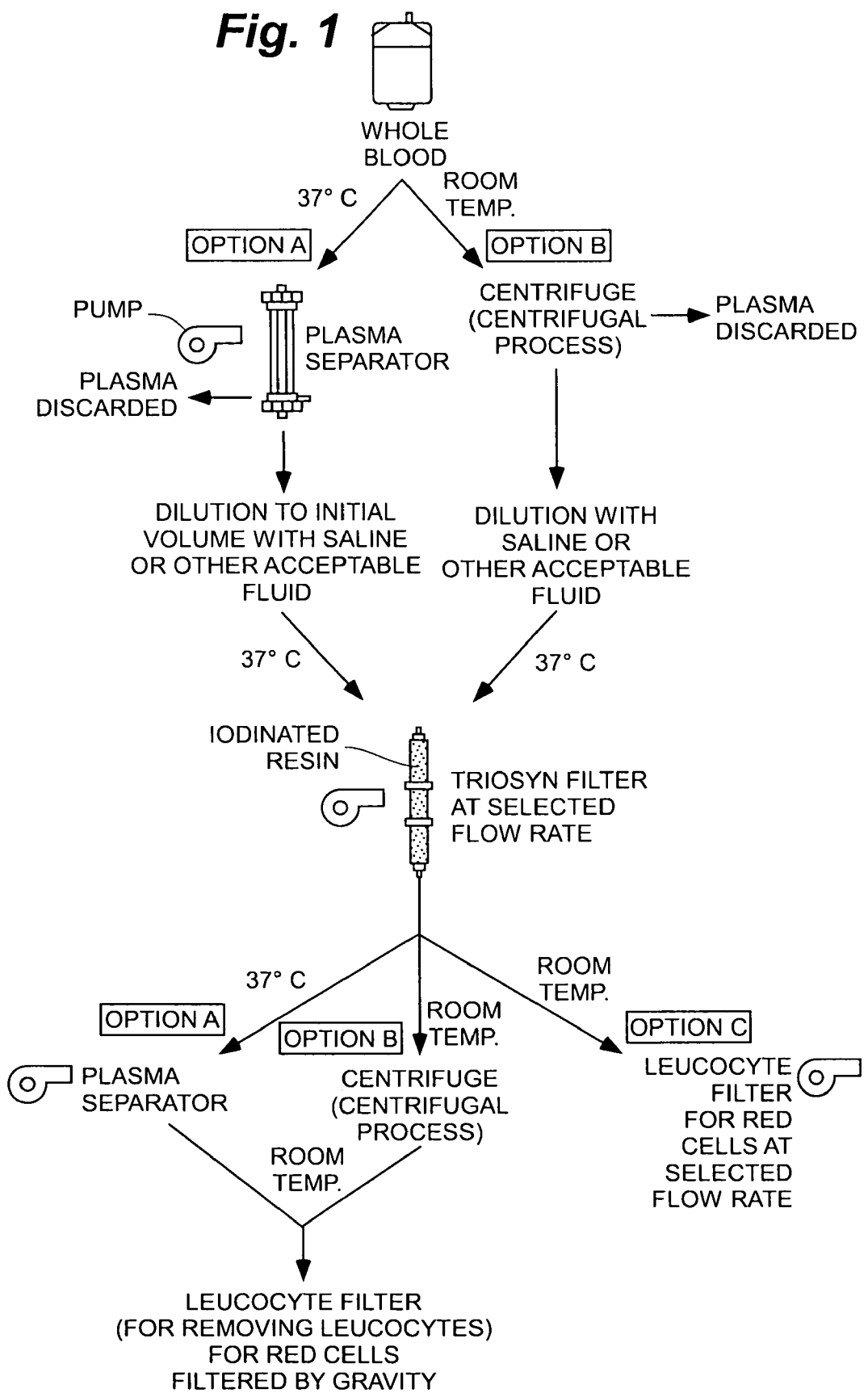
FIG. 1 depicts the Triosyn® Integrated Blood Filtration System.

The modified Triosyn.RTM. integrated blood filtration system including leukocyte removal filters, plasma separators andlor centrifugal processes in conjunction with saline or other acceptable physiological fluids comprises varying processing sequences in which the order of elements making up the filtration system may be inverted and flow rates fluctuated to obtain the most efficient biocidal reduction following the conditions of use. FIG. 1 provides a schematic description of the system. The description of pathway A (option A+option A on the schematic), which reads as follows, emphasizes the simplification of the procedure:

One unit (500 ml) of whole blood at 37° C. is filtered through a plasma separator. Plasma is discarded or treated for other use.

The red blood cell concentrate (RBC) is diluted to initial volume using saline or other acceptable physiological fluid at 37° C.

The substrate goes through the Triosyn hemoperfusion unit first and then through a plasma separator at selected flow rate (20 ml/min for instance) to be recuperated in a transfer bag.

Finally, RBC is filtrated by gravity through a leukocyte filter for leukocytes' removal and recuperated into an adequate bag or immediately transfused.

See FIG. 1. The Triosyn® Integrated Blood Filtration System

The results obtained during the last period show that the modified integrated system offers several alternatives for blood decontamination. Plasmaflo® plasma separator or centrifugation steps might be replaced in this system by any efficient mechanical plasma separation process, which allows a great flexibility to the system. In the context of battlefield operations, the full process can take place without technological support, power requirement or specialized training.

The collected blood bag can be connected to the processing filters and the flow could be activated by a hand pump to achieve full treatment.

3.2 Toxicity Profile

A first step in establishing a toxicity profile for the active ingredient of the filtration system was put in place during the first quarters of this program. A review and an analysis of the scientific literature were performed in order to determine the threshold values in view of the elaboration of the Maximum Tolerated Dose (MTD). Toxicological data gathered from the literature suggest an MTD of ionic iodine via intravenous route of 35 mg/kg or 2.5 g for an average human adult. The following formula was developed to establish the maximum blood volume and filtration time at which the MTD is attained:

Blood Volume$_{max}$=$MTD$/Iodide Concentration and Filtration Time$_{max}$=Blood Volume$_{max}$/Flow.

When considering a massive blood transfusion scenario (2.5 litres in an hour for an average human adult), residual iodide concentrations above 1000 ppm would be found to exceed the proposed MTD. Conversely, the residual iodide concentration tolerated varying on to the flow and volume of fluid transfused, the transfusion of two (2) blood units (2×500 ml) in an average man would allow residual concentrations of iodide up to 2500 ppm for a filtration time of 20 minutes.

Figure 2:
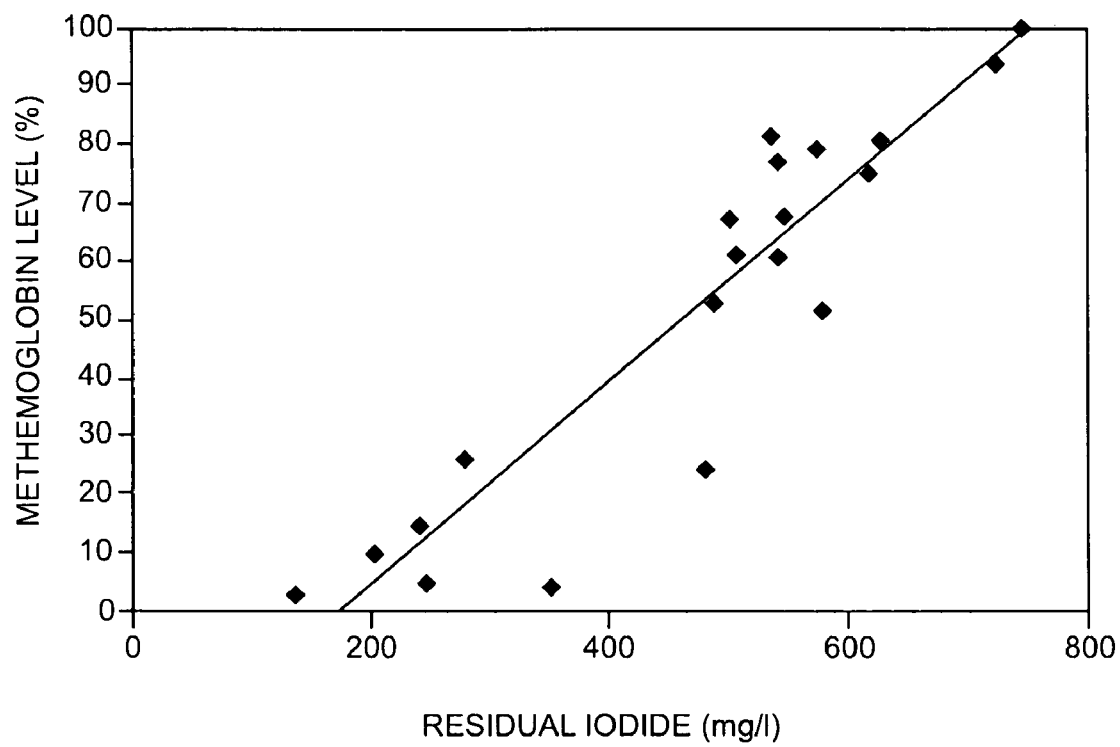
FIG. 2 depicts the correlation between residual iodide and methemoglobin levels after filtration.

The post-treatment concentration of iodide ions in blood fluids was systematically quantified in order to characterize the correlation between the state of cellular integrity and the magnitude of potential residual oxidation mechanisms in the treated blood products. Results tend to show a correlation between higher values of residual iodide, higher methemoglobin levels and more acid pH in the treated substrate. Based on these results, the assumption was made that there may be an association between higher levels of residual iodide and a more important rate of the oxidation phenomenon linked to the amount of sites that will be activated on the polymer. The more active sites will be activated on the polymer, greater the quantity of active species ($I_2^+$, HOI, $I_3^-$) that will be released, causing methemoglobin levels to rise as well as a more accentuated acidification of the milieu (substrate). FIG. 2 shows the observed correlation between the residual iodide and methemoglobin levels.

Figure 3:
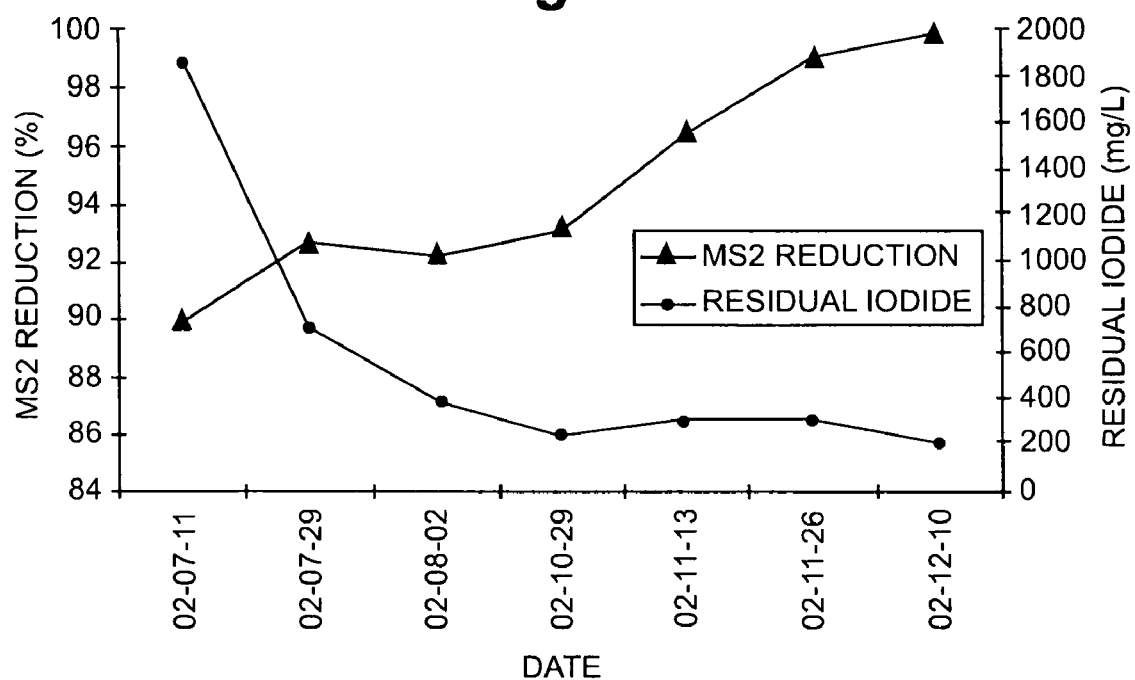
FIG. 3 depicts the progression of MS2 reduction versus residual iodide levels in blood over a 6-month testing period.
Figure 4:
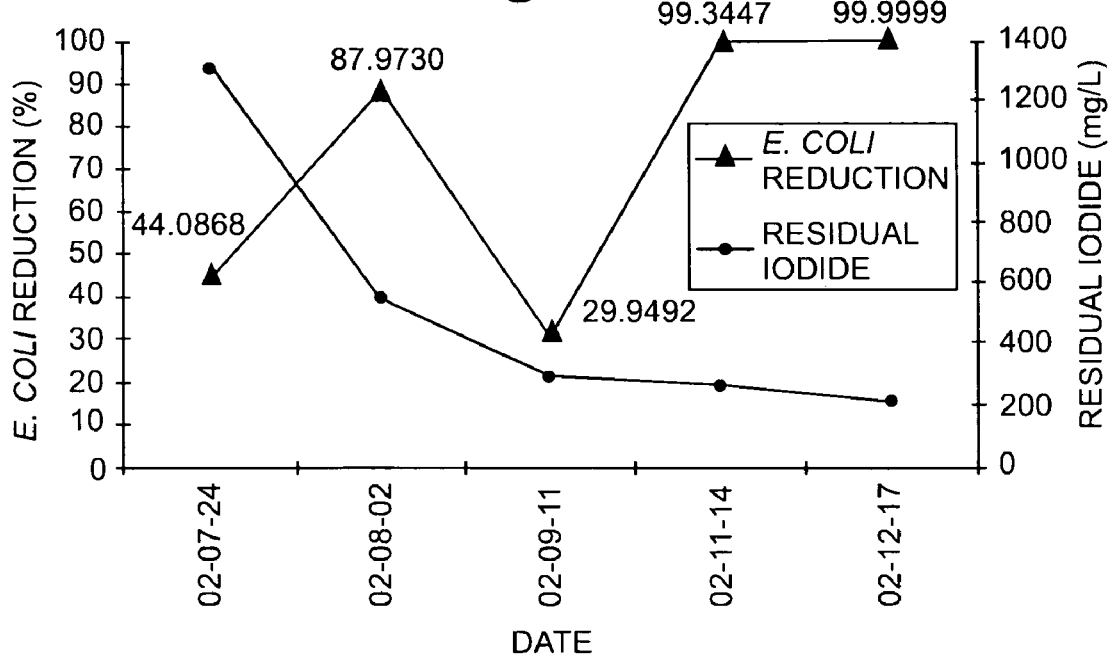
FIG. 4 depicts the progression of E. coli reduction versus residual iodide levels in blood over a 6-month testing period.
Figure 5:
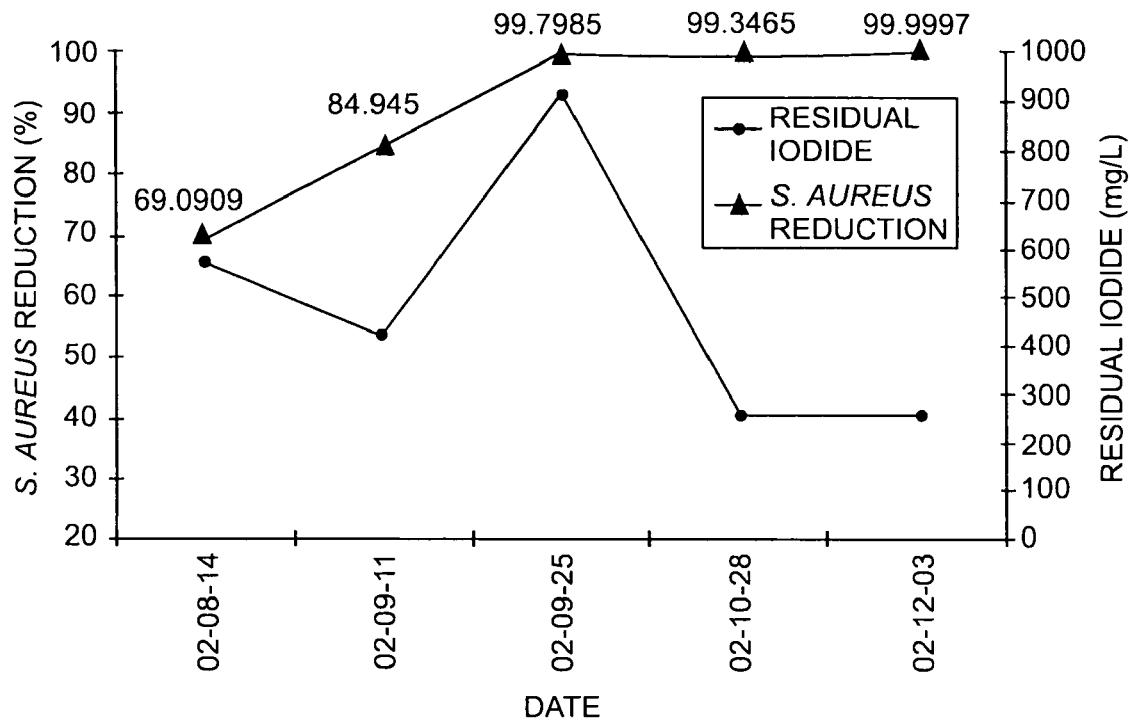
FIG. 5 depicts the progression of S. aureus reduction versus residual iodide levels in blood over a 6-month testing period.

This hypothesis is consistent with previous findings of our research suggesting a connection between the importance of the organic content of the substrate to be decontaminated and the amount of sites that will be activated on the polymer. One can suppose that the presence in the substrate of certain elements (namely erythrocytes) having specific affinities with given microorganisms will hinder effective and rapid disinfection action by preventing adequate contact with the active sites of the polymer. Such being the case, the microorganisms still present in the substrate would keep activating the demand-release mechanism causing more active complexes ($I_2^+$, HOI, $I_3^-$) to leach, resulting in higher concentrations of residual iodide. The full integrated Triosyn® system treating blood components separately allowed the achievement of important biocidal reduction in substrates with high organic content while keeping the residual iodide to low levels. As stated above, the MTD is correlated with the volume of fluid transfused as well as the flow rate of the transfusion. Under the experimental conditions prevailing for the tests presented in Table 4 (volume=500 ml and flow 50 ml/mm), residual iodide concentrations of 5000 ppm would correspond to the MTD proposed in the literature (35 mg/kg). As seen in Table 3.3, greater than 99.9% reduction was obtained against E. coli and S. aureus in RBC concentrates with a mean residual iodide level of 293.5 ppm. Up to 99.97% of MS2 viral particles were eliminated from contaminated RBC with 325 ppm or below levels of residual iodide. These values represent concentrations well below the limits of the proposed MTD of 35 mg/kg even when considering large blood volume transfusions at flow rates approximating 50 ml/mm. FIGS. 3, 4 and 5 demonstrate that, at equivalent biocidal performance, the full Triosyn® system showed lower concentration of residual iodide than prototypes selected at the end of the preceding period. These results tend to support the hypothesis that treating blood components separately will enhance contact between the microorganisms and the active sites of the polymer leading to a swifter disinfection process and minimal prompting of the demand-release mechanism.

3.3 Cellular Integrity

For the first year of the project, the main goal aimed at optimizing a first generation of prototypes able to show a satisfactory biocidal capacity all by maintaining an acceptable level of integrity for the retransfusion of the treated blood products. Considering the latter, the adopted scientific procedure expounded in previous report was planned in 3 steps. The method first consisted of obtaining a satisfactory biocidal reduction while observing the resulting effects of disinfection on the treated blood products. Secondly, it aimed at selecting and adapting the design of the prototypes such as to obtain a maximum reduction for a minimum effect on the cellular integrity. Finally, the third aspect of the project would be to consider specific mitigation measures in order to obtain treated blood products of an optimal quality.

The full integrated Triosyn® system achieves the proposed reduction objectives while keeping the observed effects on cellular integrity to a minimum.

Figure 6:
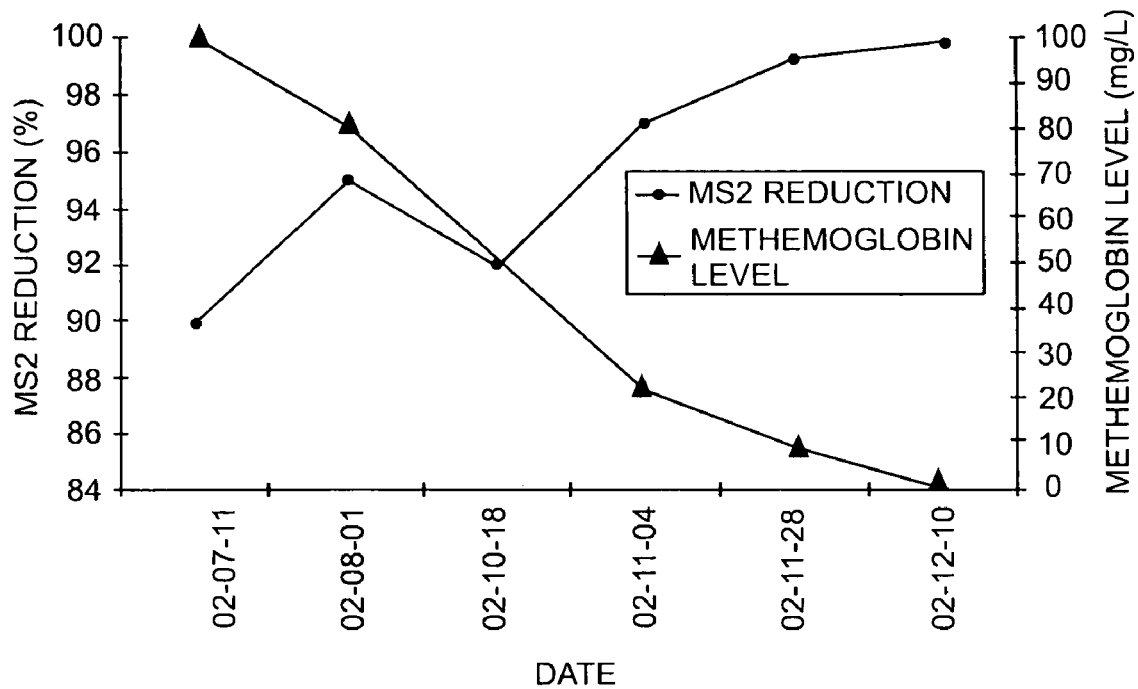
FIG. 6 depicts the progression of MS2 reduction versus methemoglobin levels in blood over a 6-month testing period.
Figure 7:
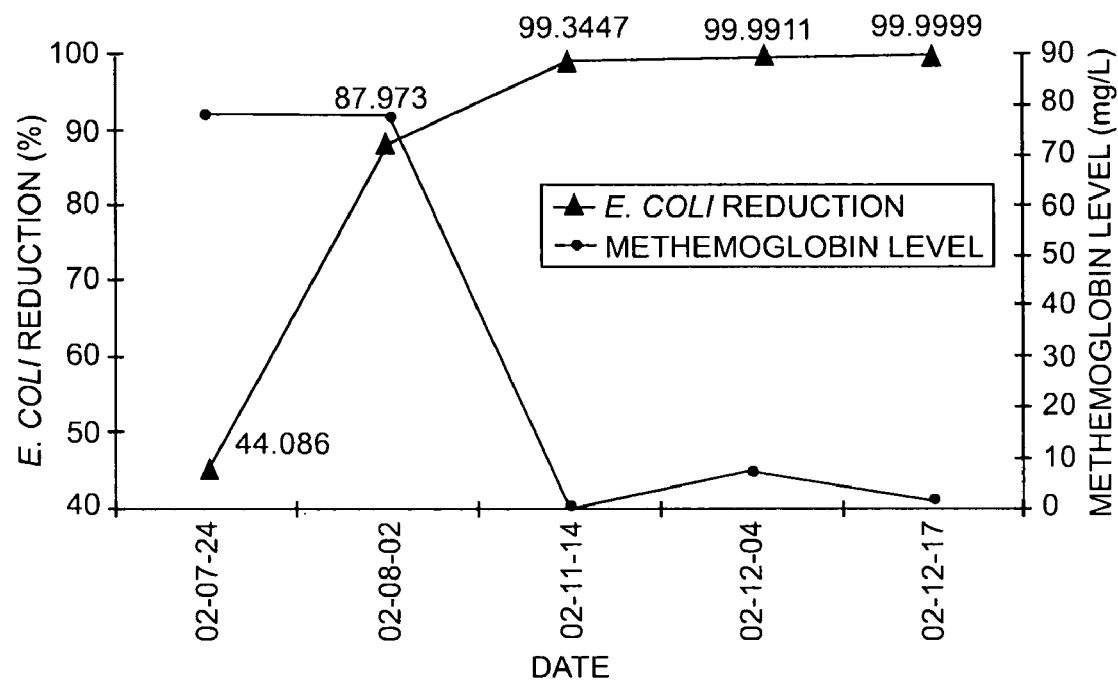
FIG. 7 depicts the progression of E. coli reduction verus methemoblogin levels in blood over a 6-month testing period.
Figure 8:
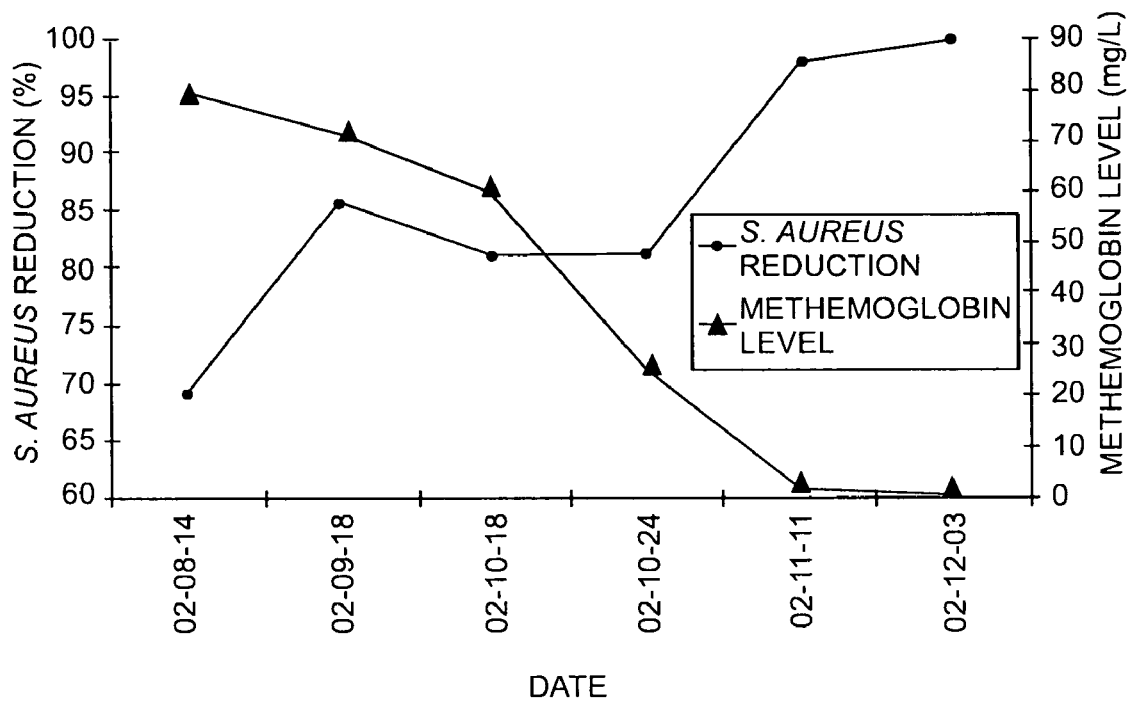
FIG. 8 depicts the progression of S. aureus reduction versus methemoglobin levels in blood over a 6-month testing period.

The in vitro analytical methods are considered as indicators allowing the prediction, to a certain extent, of the in vivo post-transfusion viability. The retained parameters were selected according to their relevance in assessing the disinfection effects of the procedure on blood cells considering the nature of the active ingredient, namely, an iodinated polymer. During Phase I of the study, the interpretation of the results was particularly based on the methemoglobin (MHb) parameter, because of its sensibility to oxidation. pH was also studied as a good indicator of the effect of the treatment on the biochemistry of the cells and the substrate. In standard RBC concentrates, the levels of methemoglobin are expected to range between 0 and 2%. Table 3.3 shows that treatment with Triosyn® integrated system, which eliminated up to 99.97% of MS2 viral particles, 99.9999% of E. coli and 99.97% S. aureus bacteria from the substrate, did not affect significantly cellular levels of methemoglobin allowing normal (between 0 and 2%) post-treatment values to be observed in RBC concentrates. FIGS. 6, 7, and 8 underscore the constant decrease in methemoglobin associated with the improvement of biocidal performance against target organisms as prototype development was progressing. The attenuation of the oxidation process of hemoglobin observed when treating RBC alone supports the assumption stated in the previous section that treating blood components separately will enhance contact between the microorganisms and the active sites of the polymer. A faster elimination of microorganisms would require smaller amounts of the active ingredient for efficient disinfection to occur.

In other respects, the oxidant nature of the active ingredient likely contributing to the somewhat acidification of the filtered substrate and provoking undesirable pH fluctuations, the addition of buffered saline, specifically adapted to the filter environment, to the substrate prior to filtration was proposed to minimize the pH fluctuations. Table 4 shows that physiological pH values between 6.89 and 7.17 were observed in RBC concentrates after treatment with Triosyn® integrated system whereas Table 3.7 brings out the specific effect of buffered saline in attenuating pH fluctuations.

TABLE 3.7 pH Fluctuations when Adding PBS or 0.85% Saline Buffer Prior to Filtration

| Buffer | Prototype Filter | Before filter | After filter | pH variation | Avg. variation |
|---|---|---|---|---|---|
| Saline 0.85% | N-BB-739 | 7.02 | 6.68 | −0.34 | −0.31 |
| | S-BB-722 | 7.05 | 6.62 | −0.43 | |
| | S-BB-723 | 7.09 | 6.78 | −0.31 | |
| | S-BB-727 | 7.15 | 6.96 | −0.19 | |
| | S-BB-735 | 7.11 | 6.82 | −0.29 | |
| PBS | N-BB-761 | 7.26 | 7.09 | −0.17 | −0.18 |
| | N-BB-762 | 7.22 | 7.06 | −0.16 | |
| | N-BB-763 | 7.12 | 6.94 | −0.18 | |
| | N-BB-766 | 7.31 | 7.11 | −0.20 | |
| | N-BB-768 | 7.34 | 7.17 | −0.17 | |

3.4 Platelets

Bacterial contamination of blood components and particularly platelets is a serious concern for the safety of the blood supply. The majority opinion in the literature is that platelets stored for the maximum time, 5 days, are more likely to be contaminated than those stored for a shorter period.

Bacterial contamination of blood components is the second largest cause of transmission related deaths in the United States, after hemolytic complications (50% of deaths), according to the FDA. Bacterial contamination causes 10% of transfusion related deaths. According to America's Blood Centers, "Bacterial sepsis is the leading microbial cause of transfusion mortality today in the United States—accounting for 46 (17%) of 277 reported transfusion deaths from 1990-1998." (3)

According to the BaCon study, as many as 10% of platelet units are contaminated with bacteria in the US. It is estimated that 1 in 10,000-20,000 units transfused in the US causes a febrile reaction due to contaminated blood (not specific to platelets) and 1 in 1-6 million units results in death. It is believed that significant transfusion reaction occurs once growth reaches the "danger zone", defined as bacterial concentrations above $10^6$ CFU/ml. (6)

The most common bacteria contaminating platelets are bacteria typically found on the skin, such as Staphylococcus spp., including S. aureus and S. epidemidis. Other bacteria include Salmonella choleraesuis, Serratia marcescens, and Bacillus cereus. (6) While most contaminations involve gram-positive skin flora, gram-negative bacteria are more frequently implicated in deaths. (3)

While conclusive evidence on how blood products become contaminated has not been collected, it is speculated that the major causes are: (6)

Donor skin at blood donation—either skin is improperly cleaned, or coring may occur at phlebotomy site.

Unapparent donor bacteremia

Contamination during collection or processing

Figure 9:
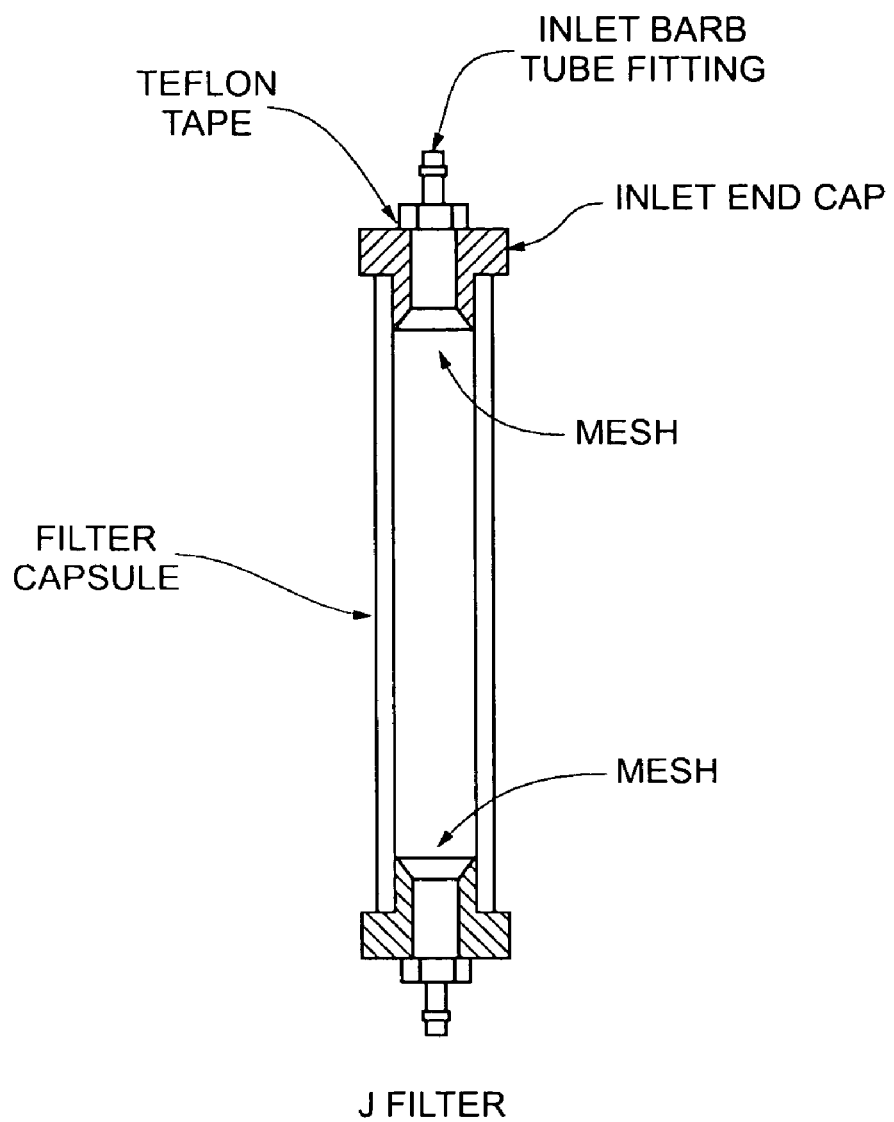
FIG. 9 depicts the Triosyn "J" filter prototype used for platelet decontamination. Characteristics of the "J" filter: Number of capsule sections: 1. Length of each capsule sections: 5'. Total length of capsule: 5'. Capsule inner diameter: 0.625'. Number of diffusers: 0. Triosyn type: iodine component can be 30-80% concentration range, preferably 35-50%. Volume of Triosyn: 25 g. Triosyn size: 500 microns.
Figure 10:
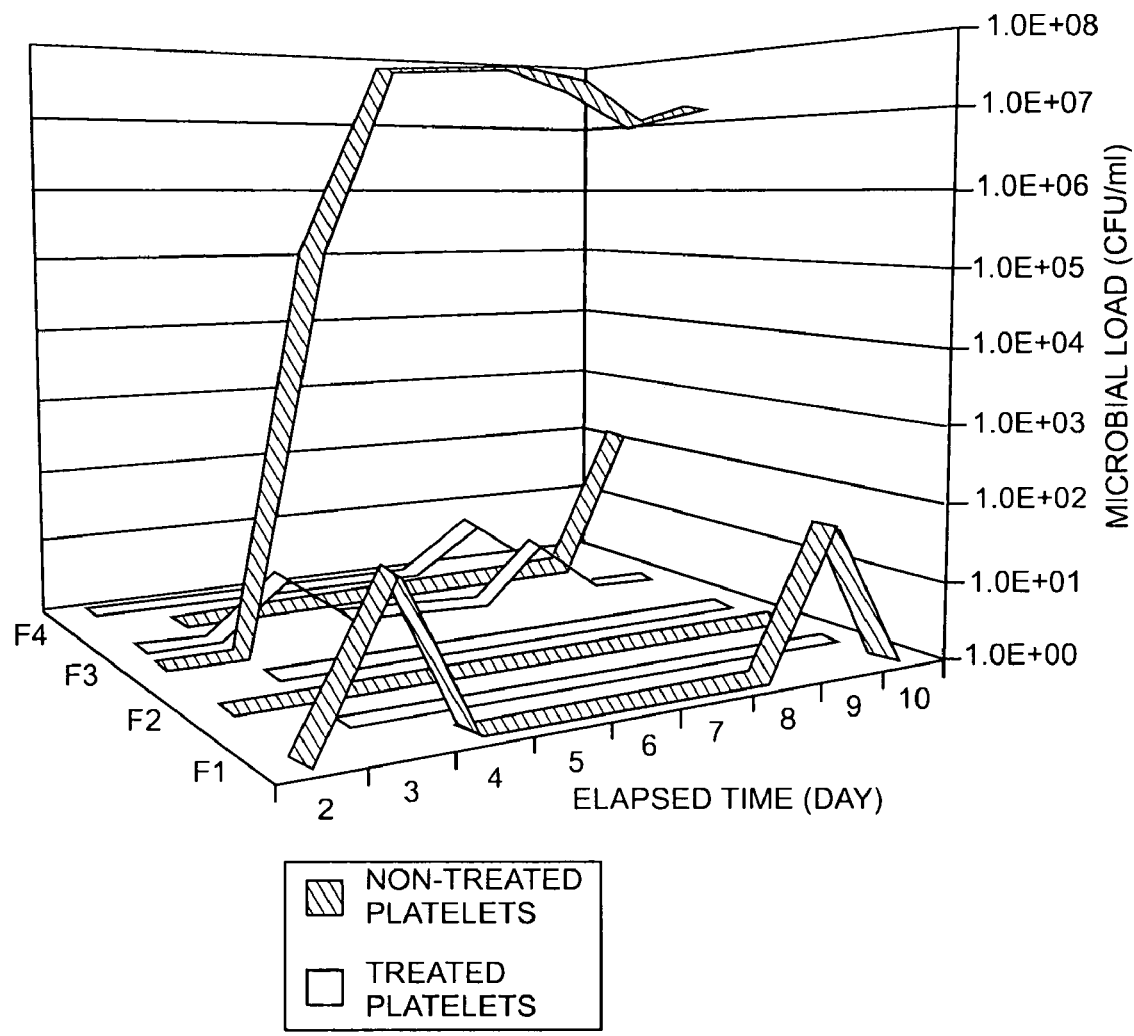
FIG. 10 depicts the evolution of bacterial load over time in treated vs. non-treated platelets.
Figure 11:
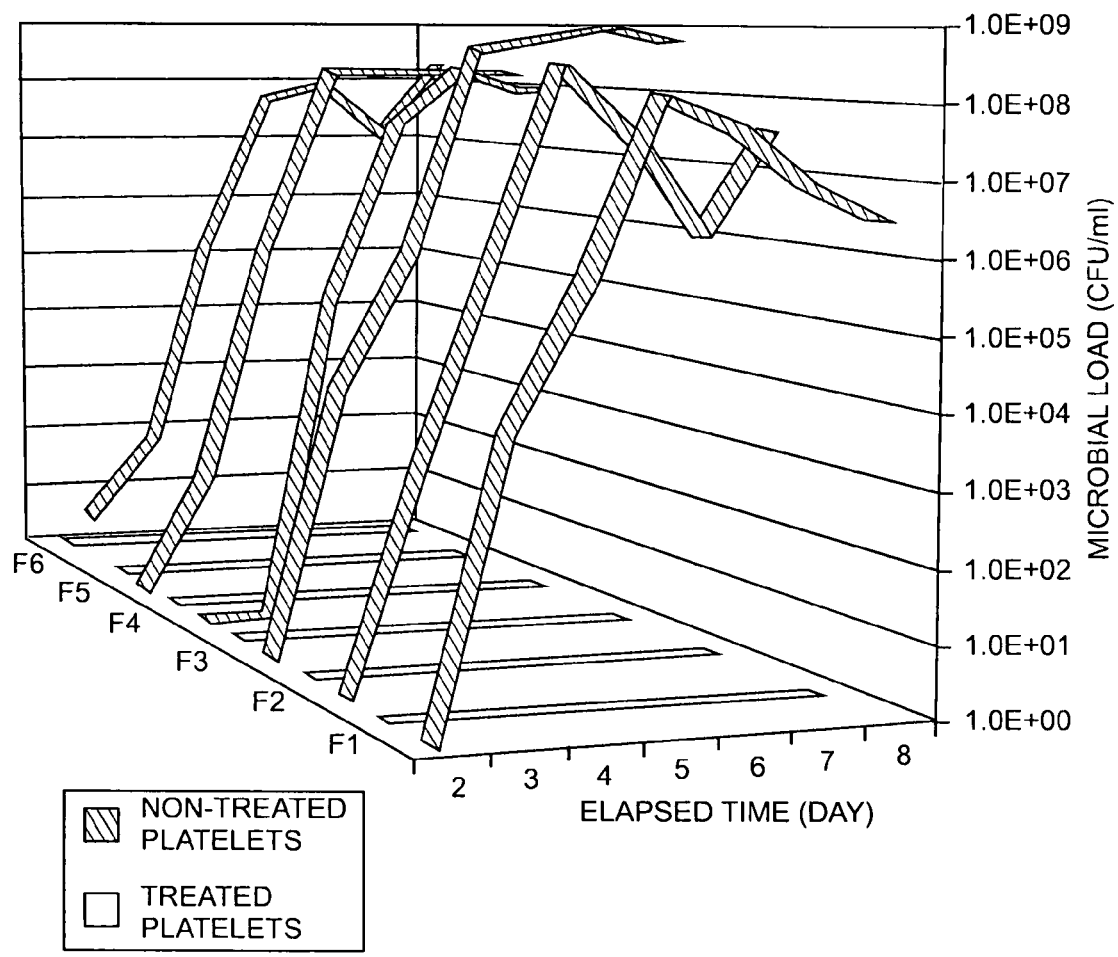
FIG. 11 depicts the evolution of Staphylococcus aureus concentration over time in treated vs. non-treated platelets.
Figure 12:
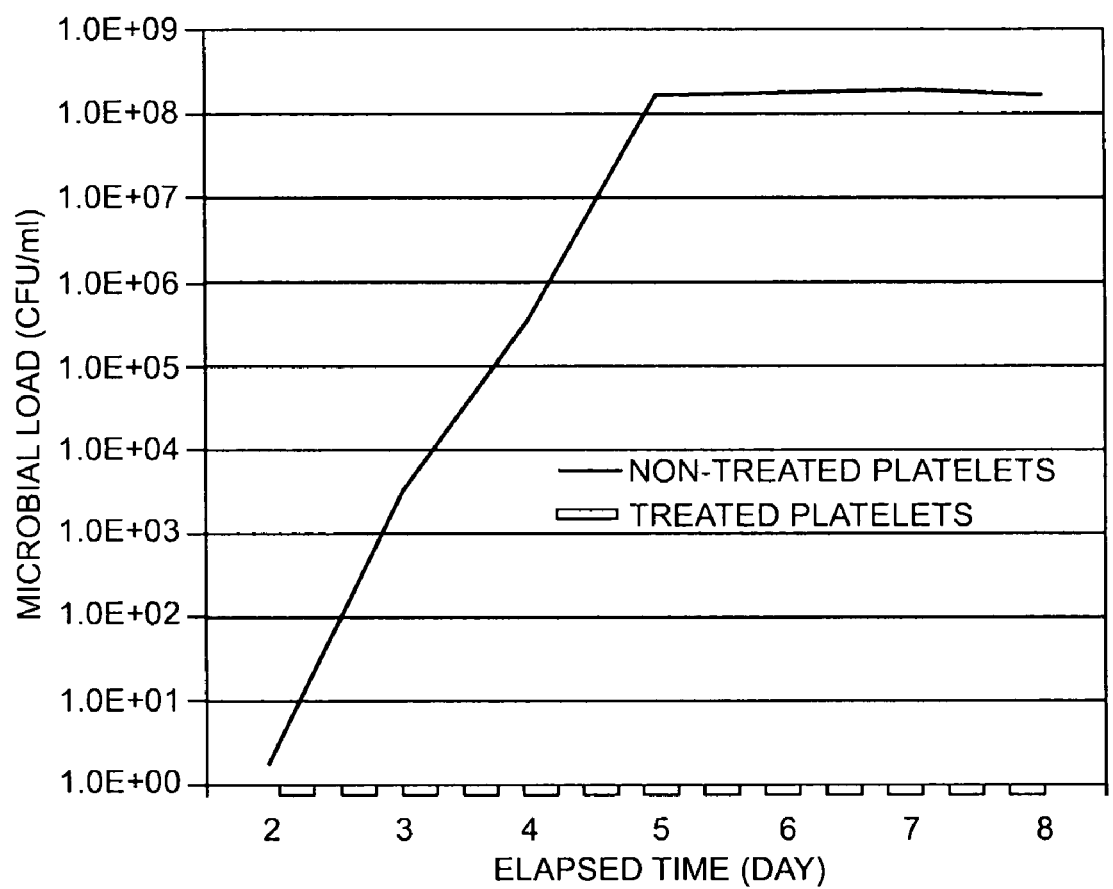
FIG. 12 depicts the average evolution of Staphylococcus aureus concentrations over time in treated vs. non-treated platelets, where n=6.

In the wake of the tests performed on the different components of blood, a series of preliminary experiments were conducted on the filtration of platelet concentrates. Although the current gold standard of clinical platelet efficacy is in vivo survival of transfused radio-labelled platelets, the use of in vitro tests is accepted in the first stages of R&D as a screening process to eliminate inadequate procedures or develop innovative treatment without requiring human trials (62). Within these initial tests, the morphology, pH and bacterial contamination status of platelet concentrates were observed before and after procedure. The treatment simply consists in processing platelet units (prepared as per standard procedure and diluted to obtain sufficient volume) through a Triosyn column, as illustrated in FIG. 9, at a flow rate of 10 ml/min. The platelets are directly collected in a transfer bag used for storage.

The following figures allow the observance of the evolution of bacterial load on a timeframe of ten (10) days in the case of filtered vs. non-filtered platelets. These observations were noted on control units of platelets as well as units that were contaminated with a strain of Staphylococcus aureus ($10^2$ CFU).

Bacterial growth was detected in 3 platelet units (F1, F3 & F4) in which the growth pattern was consistent with cross-contamination due to manipulation (no sustainable growth over time in the sample, no growth in lower dilutions). However, bacterial load rose to high concentrations from day 3 in one non-treated unit (F3) whereas an upward trend was detectable from day 8 in F4 non-treated platelets.

the medium, bacteria growth attains a plateau or slightly regresses. On the other hand, no bacterial growth was observed in the filtered units.

TABLE 3.8 pH Values Observed in Treated and Non-Treated Platelets

|  | Sample | pH Day 2 | pH Day 5 | pH Day 6 | pH Day 7 | pH Day 8 |
|---|---|---|---|---|---|---|
| Control | F1 | 7.36 | 7.53 | 7.26 | 7.18 | 6.78 |
|  | F2 | 7.37 | 7.57 | 7.28 | 7.14 | 7.12 |
|  | F3 | 7.22 | 7.30 | 6.90 | 6.78 | 6.64 |
|  | F4 | 7.49 | 7.34 | 7.15 | 7.12 | 7.09 |
|  | F5 | 7.40 | 6.96 | 6.91 | 6.90 | 6.97 |
|  | F6 | 7.08 | 7.07 | 6.87 | 6.91 | 6.66 |
| Treated | F1 | 7.04 | 7.75 | 7.81 | 7.90 | 8.05 |
|  | F2 | 7.08 | 7.81 | 7.91 | 8.06 | 8.26 |
|  | F3 | 6.97 | 7.75 | 7.80 | 7.89 | 7.99 |
|  | F4 | 7.16 | 7.48 | 7.56 | 7.77 | 7.85 |
|  | F5 | 7.03 | 7.23 | 7.40 | 7.53 | 7.55 |
|  | F6 | 7.08 | 7.34 | 7.44 | 7.61 | 7.68 |

Table 3.9 presents the morphological score noted following microscopic observation of the platelets. Overall, the results emphasize the preservation of the cellular integrity within the filtered platelets while the non-treated units present a rapid degradation within the platelet's morphologic state with the progression of morphologic changes from the usual discoid shape to spherical, dendritic and balloon shapes, characteristic of activated platelets.

TABLE 3.9

Changes Noted in Morphological Score of Treated and Non-treated Platelets

|  | Sample | Morphological Score Day 2 | Morphological Score Day 5 | Morphological Score Day 6 | Morphological Score Day 7 | Morphological Score Day 8 |
|---|---|---|---|---|---|---|
| Control | F1 | B | C | D | D | D |
|  | F2 | A | D | D | D | D |
|  | F3 | B | C | C | C | C |
|  | F4 | B | D | D | D | D |
|  | F5 | B | D | D | D | D |
|  | F6 | B | D | D | C | D |
| Treated | F1 | A | A | A | A⁻ | A |
|  | F2 | A | A | A | A | B |
|  | F3 | A | B | B | B | B |
|  | F4 | A | A | A | A | A |
|  | F5 | A | A | A | A⁻ | A |
|  | F6 | A | B | B | B | B |

The results show the capacity of the filters in eliminating the inoculated microbial agent such as to prevent further proliferation. In contrast, an increase in the bacterial load resulting in high concentrations ($10^8$ CFU/ml) of Staphylococcus aureus was noted for all the non-treated units.

The average curve illustrates the exponential bacteria growth observed in the non-treated platelet units during the 4 days following contamination. This growth phase is accompanied by an acidification of the medium as evidenced by the pH values presented in table 3.8. Following the exhaustion of Based on FDA recommendations, the lactate dehydrogenase (LDH) and lactate levels in the medium were measured to pursue the in vitro evaluation of platelet biochemistry.

Literature reports that a decrease in platelet count with an increase of LDH level in the medium can be used as an indicator of platelet lysis. LDH levels and platelet counts were analyzed and compared before and after treatment over a six-day period. The platelets units have been treated on day 2 and LDH levels determined before and after treatment on day 2, 3, 4, 5 and 6.

Figure 13:
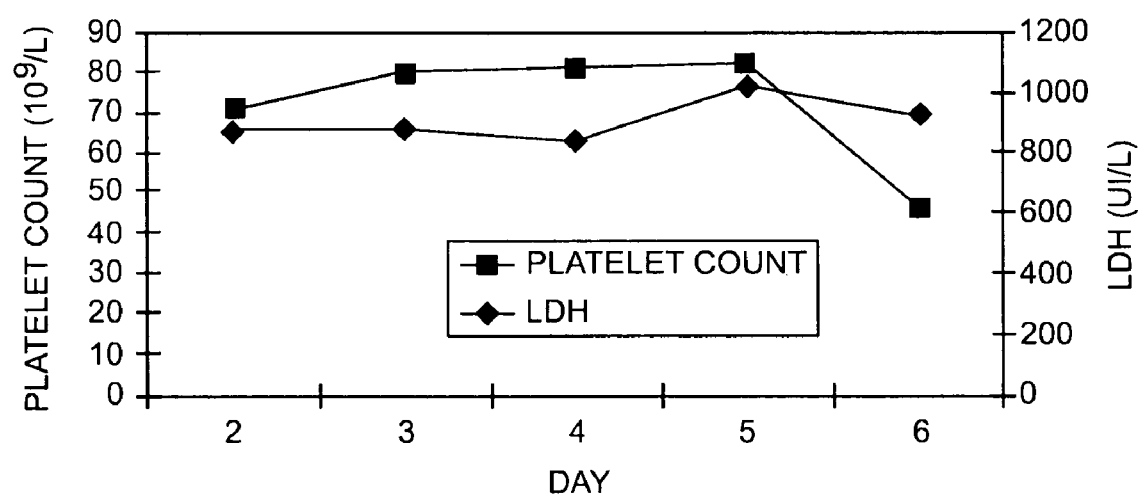
FIG. 13 depicts the correlation between Lactate Dehydrogenase (LDH) levels and platelet counts in control samples over a six-day period.
Figure 14:
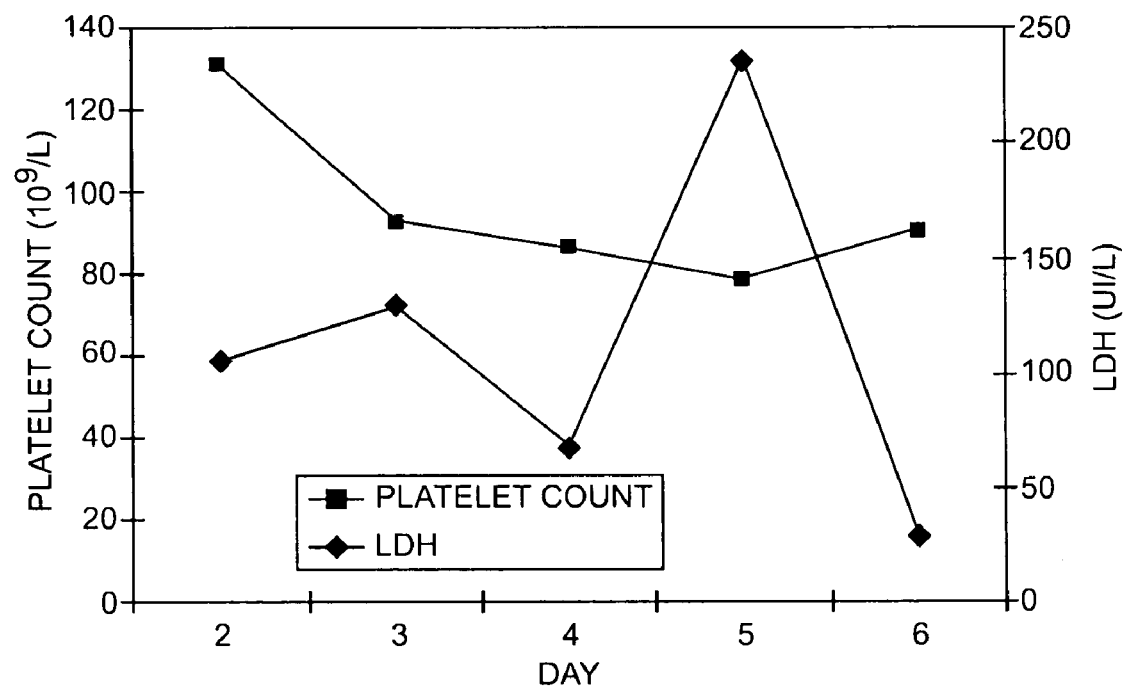
FIG. 14 depicts the correlation between Lactate Dehydrogenase (LDH) levels and platelet counts in treated samples over a six-day period.

FIGS. 13 and 14 allow the comparison of results obtained from treated versus control platelet units.

In control samples, the platelet count was found to be relatively constant up to day 5. A decrease in platelet count was then observed after day 6. In parallel, the levels of LDH were found to be constant, and then were followed by an increase on day 5 and a decrease on day 6 suggesting the occurrence of platelet lysis on day 5.

The same phenomenon occurred for treated platelet units on day 3 of testing; specifically, the level of LDH increased on day 3, and then decreased on day 4. However, despite a significant increase of the LDH level on day 5, the platelet count seemed to remain relatively constant until the end of storage. Therefore, an increase of the latter cannot be correlated to platelet lysis. It could, however, be explained by the presence of an interference. The presence of citrate in the media is often responsible for interfering with the actual readings of free LDH.

Figure 15:
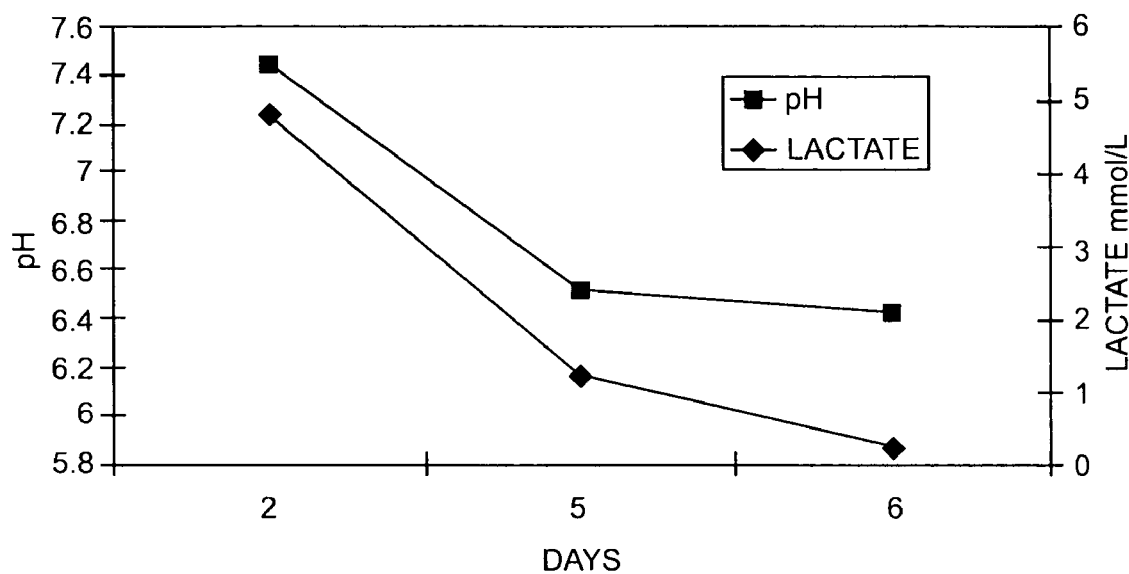
FIG. 15 depicts the correlation between Lactate and pH levels in control samples over a six-day period.
Figure 16:
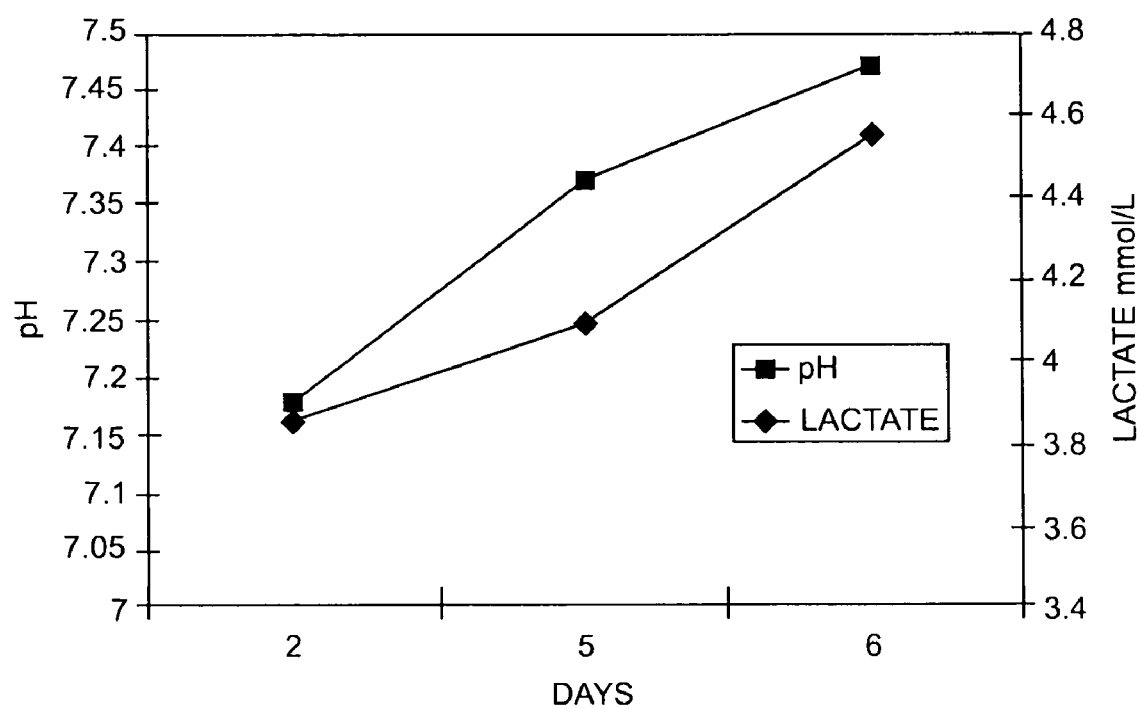
FIG. 16 depicts the correlation between Lactate and pH levels in treated samples over a six-day period.
Figure 17:
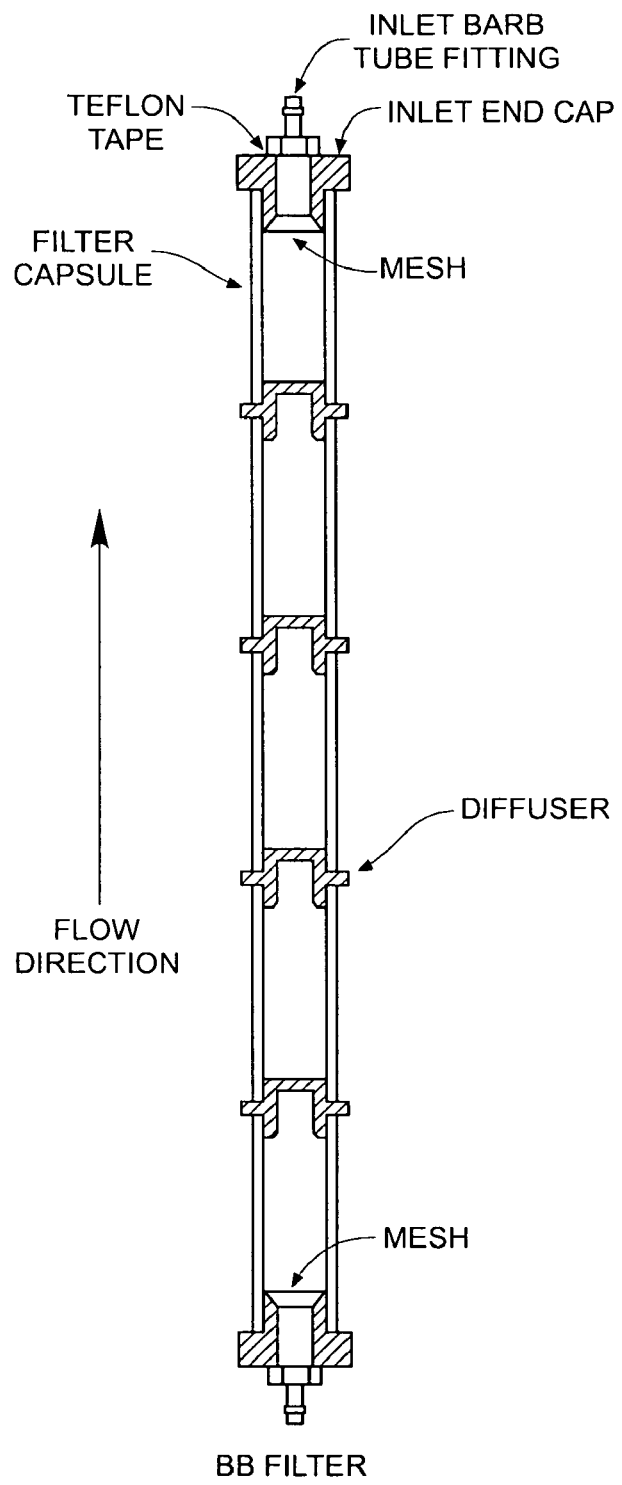
FIG. 17 depicts the characteristics of the "BB" filter. Characteristics of the "BB" filter: Number of capsule sections:5. Length of each capsule sections: 2.75'. Total length of capsule: 13.75'. Capsule inner diameter: 0.75'. Number of diffusers: 4. Triosyn type: iodine component can be 30-80% concentration range, preferably 35-50%. Volume of Triosyn: 100 g. Triosyn size: 500 microns.
Figure 18:
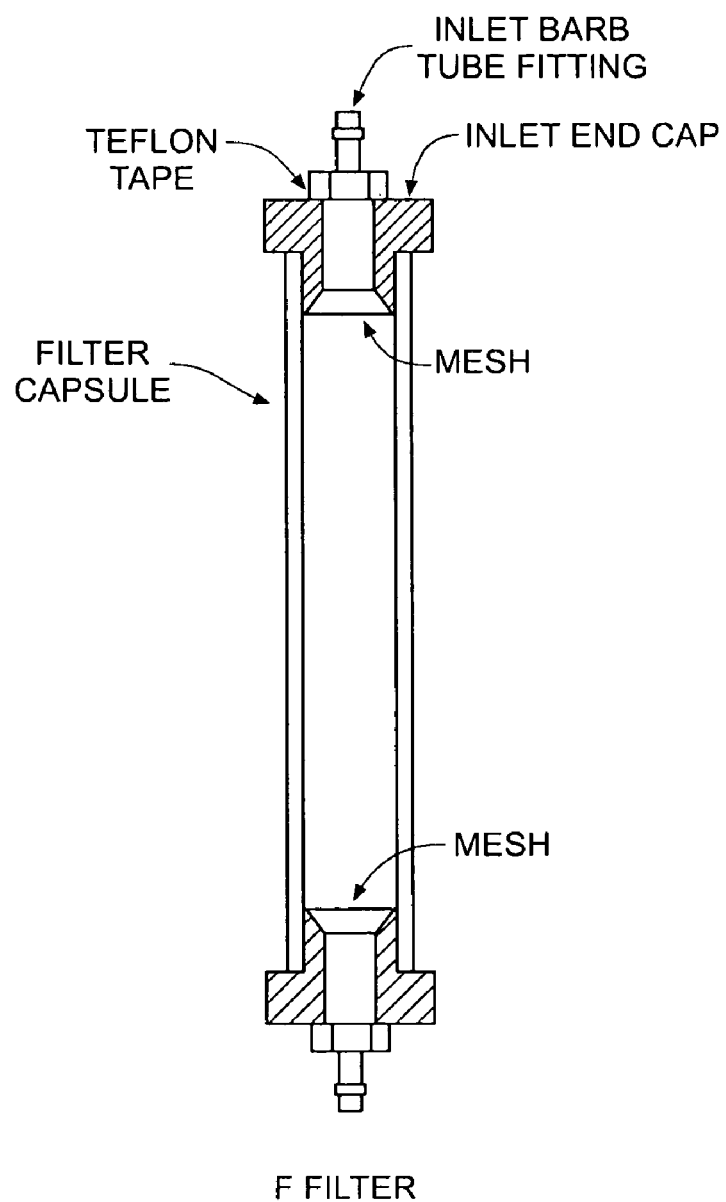
FIG. 18 depicts the characteristics of the "F" filter. Characteristics of the "F" filter: Number of capsule sections: 1. Length of each capsule sections: 6'. Total length of capsule: 6'. Capsule inner diameter: 0.75'. Number of diffusers: 0. Triosyn type: iodine component can be 30-80% concentration range, preferably 35-50%. Volume of Triosyn: 45 g. Triosyn size: 500 microns.
Figure 19:
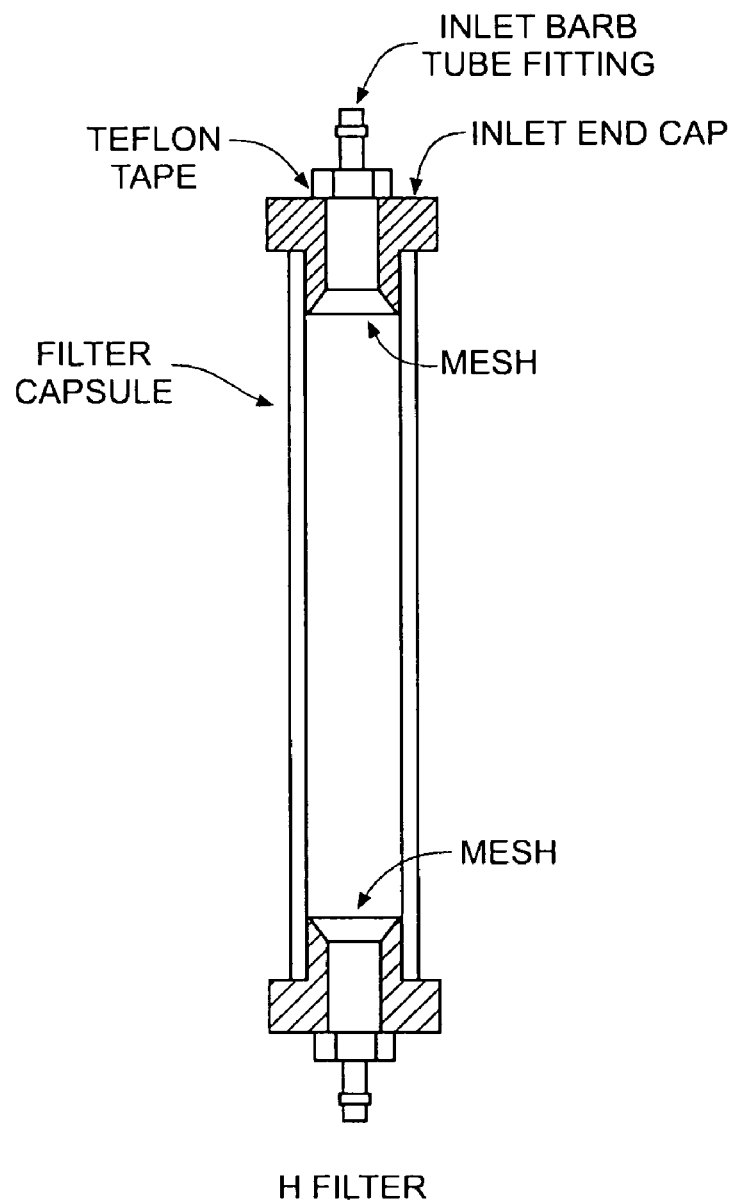
FIG. 19 depicts the characteristics of the "H" filter. Characteristics of the "H"filter: Number of capsule sections: 1. Length of each capsule sections: 5'. Total length of capsule: 5'. Capsule inner diameter: 0.625'. Number of diffusers: 0. Triosyn type: iodine component can be 30-80% concentration range, preferably 35-50%. Volume of Triosyn: 25 g. Triosyn size: 500 microns.
Figure 20:
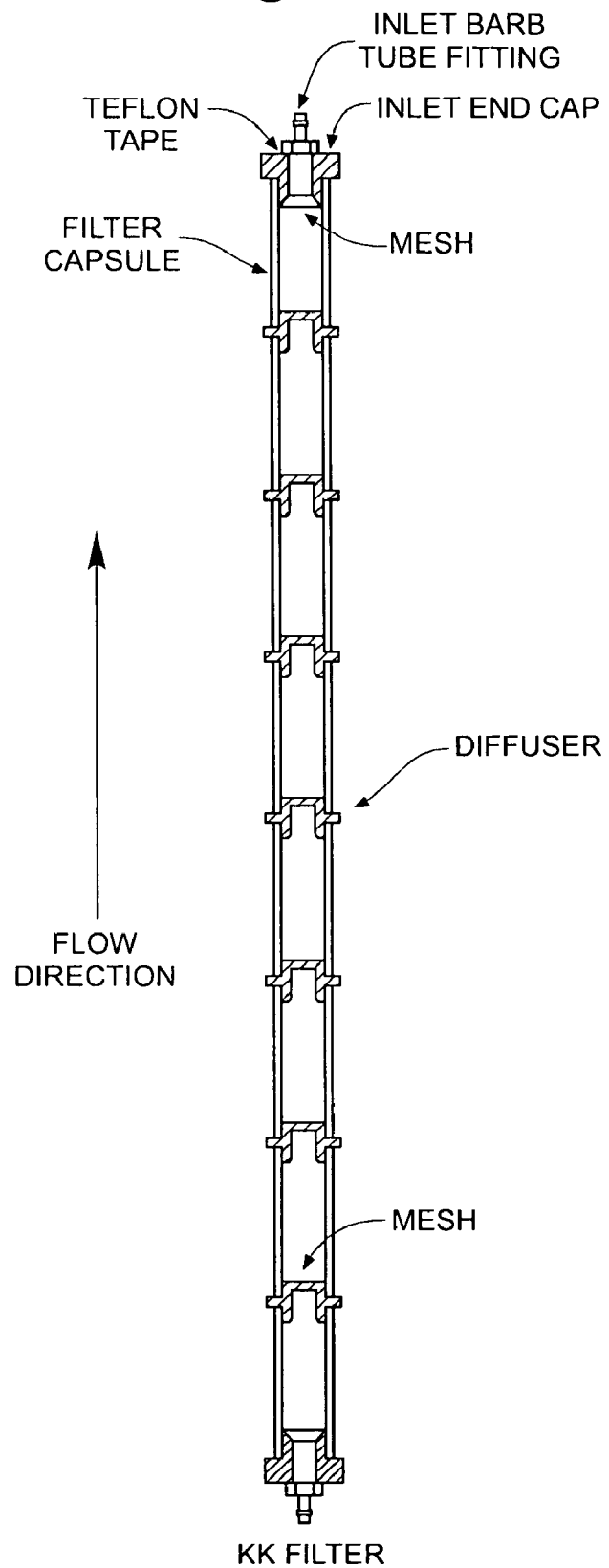
FIG. 20 depicts the characteristics of the "KK" filter. Characteristics of the "KK"filter: Number of capsule sections:8. Length of each capsule sections: 2.75' and 1.38' for the first. Total length of capsule: 20.63'. Capsule inner diameter: 0.75'. Number of diffusers: 7. Triosyn type: iodine component can be 30-80% concentration range, preferably 35-50%. Volume of Triosyn: 500 g. Triosyn size: 500 microns.
Figure 21:
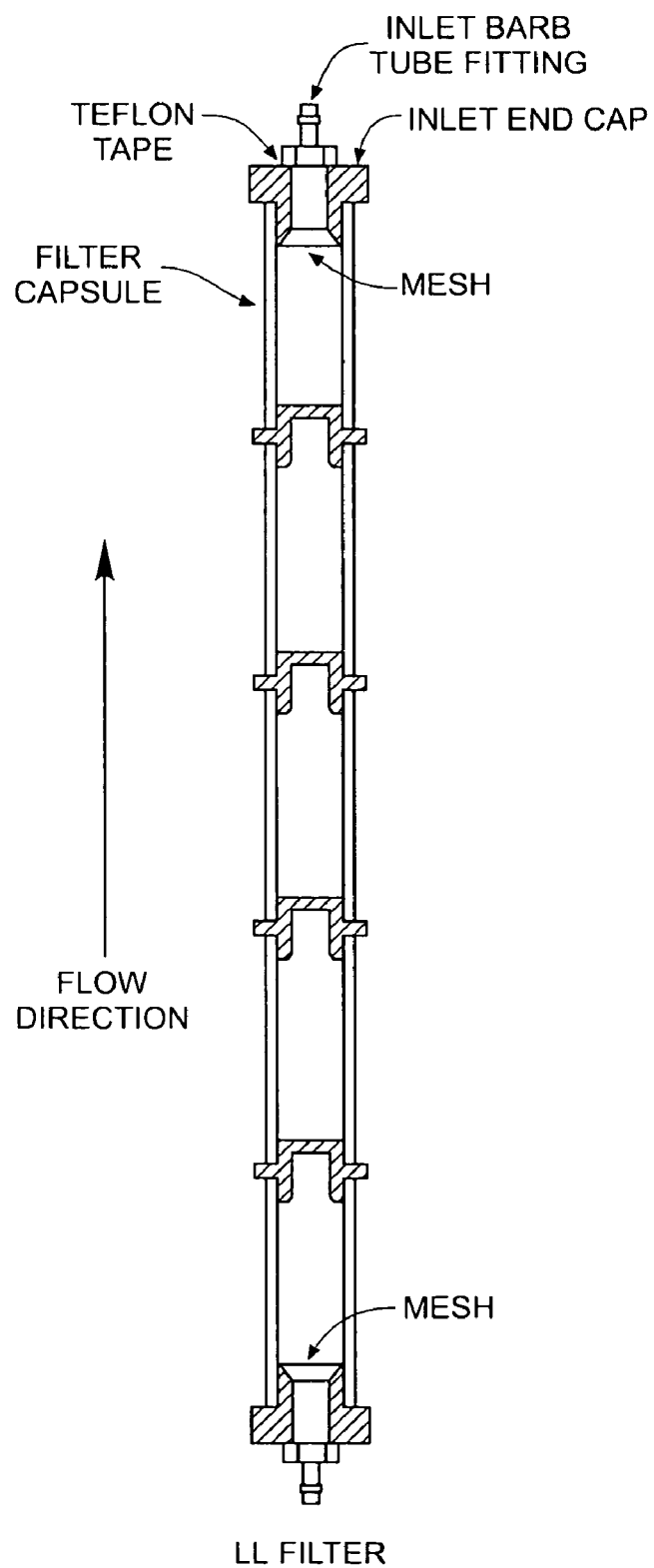
FIG. 21 depicts the characteristics of the "LL" filter. Characteristics of the "LL"filter: Number of capsule sections:5. Length of each capsule sections: 2.25' and 1.31' for the first.

The lactate and pH levels were also determined for treated and control samples on day 2, 5 and 6 as seen in FIGS. 15 and 16 [3.15 and 3.16].

A decrease in the pH level was observed between day 2 and day 5 in control samples in parallel with a loss of platelet viability, which could explain the critical decrease in platelet counts. Plasma is known to contain coagulation factors, enzymes and complements. These factors may trigger platelet activation and subsequently platelet lysis during storage, therefore leading to a decrease in platelet counts. In that event, it is not abnormal to observe a decrease of lactate levels over time. A decrease in platelets is often associated with a glycolysis decrease, which is then followed by a lactate production decrease.

Usually, an accumulation of lactate due to glycolysis is observed at a rate of 2.5 mM/day. A normal increase of lactate levels was observed over time in treated platelets. An initial decrease in the platelet count was observed the day after treatment occurred to reach a plateau and remain stable throughout the storing process. It was hypothesized that this diminution in platelet counts might be reflecting a loss of activated platelets, which would be mechanically retained by the filter, contributing to improve the condition of remaining sound platelets over the storage period.

Using LDH and lactate as testing parameters for in vitro evaluation of platelet biochemistry, it is possible to conclude that platelet units seemed to be preserved longer when filtrated with Triosyn® units than the ones without treatment.

These preliminary findings suggest that the filtration of platelet units with an interactive broad-spectrum biocidal polymer may help in preventing bacterial contamination of platelet concentrates and preserve the integrity of the cells.

3.5 Leukodepletion

Due the possible adverse immune reactions they can cause, white blood cells (leukocytes) are not desired components of blood products for transfusion. Thus, embodiments of the Triosyn® filtration system utilizes leukocyte removal filters, such as those made commercially available by Leukotrap®, Pall Corporation, East Hills, N.Y. 11548, USA and Sepacell®, Baxter Healthcare Corp, Il, USA. The leukocyte removal filter may be situated within the Triosyn® filtration system in different sequences (before or after the Triosyn® unit).

The manufacturers of Leukotrap® and Sepacell® filters guarantee a 99.95% reduction of leukocytes in the blood. The reduction standard based on applicable federal statutes and regulations of the Food and Drug Administration (FDA), US Department of Health and Human Services requires leukodepleted products to show $<5 \times 10^6$ leulocytes/unit counts. The effectiveness of leukocyte removal under the actual conditions of use and the physical configuration of the decontamination system had to be demonstrated.

The counting of leukocytes in red cell products (34, 36, 54 and 63) is based on a conventional method. This counting method describes a procedure for visual counting of leukocytes present in leukodepleted blood. The method uses a Nageotte counting chamber with 2 50 ul-grid. The sensitivity of the method is 0.1 leukocyte/ul and should be used only in products for which leukodepletion has reduced the count to levels below 5 leukocytes/ul. See Table 3.10.

TABLE 3.10

White Cell Counts in Red Blood Cells Leukodepleted with Sepacell ® Filters

| | No Nutricell added | | | 100 ml Nutricell added | |
| --- | --- | --- | --- | --- | --- |
| Sample | WBC before Sepacell cells/L | WBC after Sepacell cells/L | % reduction | WBC after Sepacell cells/L | % reduction |
| N-BB-769 | 1.06E+10 | 2.41E+07 | 99.77 | 7.48E+06 | 99.93 |
| N-BB-770 | 8.10E+09 | 1.49E+07 | 99.82 | 3.53E+06 | 99.96 |
| N-BB-771 | 7.10E+09 | 2.67E+07 | 99.62 | 7.50E+06 | 99.89 |
| 021216-37-4 | 6.30E+09 | 8.10E+06 | 99.7 | 3.20E+06 | 99.95 |
| 021216-61-7 | 7.30E+09 | 8.00E+06 | 99.89 | 2.80E+06 | 99.96 |

Advantages

Some advantages and accomplishments of the present invention include the following:
- Demonstrated reproducible biocidal capacity exceeding 99.9% in the eradication of MS2 viral particles, *E. coli* and *S. aureus* bacteria from RBCs suspensions.
- Up to 99.97% reduction of MS2 viral particles in red blood cell concentrates with maintenance of normal methemoglobin level and physiological pH.
- Up to 99.9999% reduction of *E. coli* concentration in red blood cell concentrates with maintenance of normal methemoglobin level and physiological pH.
- Up to 99.97% reduction of *S. aureus* concentration in red blood cell concentrates with maintenance of normal methemoglobin level and physiological pH.
- Achievement of >99.9% biocidal reduction (including viruses and bacteria) while keeping residual iodide levels well below the limits of the Maximum Tolerated Dose (35 mg/kg) considering a massive transfusion scenario (2.5 L in an hour).
- Prevention of bacterial proliferation in platelet concentrates with preservation of cellular integrity.
- Increased storage time (up to 10 days) of platelets without bacterial degradation.

Experimental demonstration of elimination of *Staphylococcus aureus* inoculated in platelet samples with no observable adverse affects.

Integration of effective leukocyte depletion to the filtration system according to FDA standard (<$5\times10^6$ leukocytes/unit).

Improvement of portability and adaptability of Triosyn® integrated blood filtration system while maintaining biocidal performance and minimal impact on cellular integrity.

CONCLUSION

Considering the variations observed in the biocidal reduction according to the type of substrate filtrated and based on the fact that blood components are usually administered separately in current transfusion practices, an integrated Triosyn® filtration system was developed for separate treatment of blood components. The integrated system includes commercially available leukocyte filters which proved to be efficient under the actual conditions of use and the physical configuration of the decontamination system. During previous quarters, reduction objectives of 99% were exceeded in plasma and serum with, respectively, up to 99.9978% and greater than 99.9999% reduction of MS2 viral particles and *E. coli*. The development of the integrated system allowed for a reproducible biocidal reduction rate greater than 99.9% against MS2 viral particles and *S. aureus* bacteria in presence of erythrocytes (RBC concentrates) whereas bacterial reduction of up to 99.9999% was obtained against *E. coli*. The increase obtained in terms of microbiological reduction within this system is all the more significant since it is associated with a considerable reduction of the impacts observed on cellular integrity. Normal levels of methemoglobin (between 0 and 2%) and physiological values of pH were maintained in RBC concentrates after treatment with Triosyn® integrated system. The examination of the progression of biocidal reduction versus residual iodide levels in blood over the last 6-month testing period showed that, for equivalent biocidal performance, the full Triosyn® system showed lower concentration of residual iodide than prototypes selected at the end of the preceding period, i.e. values representing concentrations well below the limits of the proposed MTD (325 ppm or below vs 5000 ppm treshold).

Detail of Triosyn Filter Unit

FIGS. 4-9 depict exemplary embodiments of different types of filter units/hemoperfusion units (namely BB, F, H, KK, LL and O, respectively) that may be used within the present invention.

The specific characteristics of both the column and the iodinated polymer for each type of filter are included in the respective drawings.

Exemplary Process Flows

In accordance with the present invention, the following section entitled "Triosyn Blood Technology" describe integrated processes for purification of blood and blood components using iodinated resin, leukocyte removal filters, fluid separators and/or centrifugal processes in conjunction with saline or other acceptable physiological fluids. Processing sequences may be varied, that is, the order of elements making up the filtration system may be inverted and flow rates fluctuated to obtain the most efficient biocidal reduction following the conditions of use.

APPLICATION

FIG. 23 depicts a top view and cross sectional view of the diffusers used within the filter units/hemoperfusion units. FIGS. 24 and 25 depict alternative battlefield transfusion scenarios using two embodiments of the Triosyn purification system. FIGS. 26 and 27 depict processes of cleansing/purifying the blood of viruses such as the SAR virus and the AIDS virus, within a human using two embodiments of the Triosyn purification system.

APPENDICES

The accompanying Appendices also form part of this disclosure.

REFERENCES

1. Adams G A, Swenson S D, Rock G. 1986. Survival and recovery of human platelets stored for five days in a non-plasma medium. Blood, vol. 67:3 pp. 672-675.
2. American Association of Blood Banks, America's Blood Centers and the American Red Cross. (August 2000) Circular of Information for the use of human blood and blood components., pp. 1-32.
3. America's Blood Centers. "Bacterial Contamination of Blood Components" July 2000. Online at: http://66.155.15.152/medical/bulletin_v3_n2.htm
4. Amy D. Shapiro, M. D., Indiana Hemophilia and Thrombosis Center, Indianapolis, U.S.A. (1999) Platelet Function Disorders. Treatment of Hemophilia Monograph Series, Number 19. World Federation of Hemophilia: pp. 1-11.
5. Arthur P. Bode. (1990) Platelet Activation May Explain the Storage Lesion in Platelet Concentrates., Blood Cells (1990) vol. 16: pp. 109-126.
6. "Assessment of the Frequency of Blood Component Bacterial Contamination Associated with Transfusion Reaction (BaCon Study)," American Association of Blood Banks, American Red Cross, CDC, Department of Defense. Available online at http://www.cdc.gov/ncidod/hip/bacon/index.htm
7. AuBuchon J P; Dodd R Y. 1992. Inactivation of Microbial Contaminants of Blood Components. Clin Lab Med, vol. December 12:4, pp. 787-803.
8. AuBuchon J P.; Elfath M D.; Popovskyk M A.; Stromberg R R.; Pickard C.; Herschel L.; Whitley P.; McNeil D.; Arnold N.; O'Connor J L. 1997. Evaluation of a new prestorage leukoreduction filter for red blood cells. Vox Sang, vol. 72, pp. 101-106.
9. AuBuchon J P.; Pickard C.; Herschel L.; O'Connor J L. Documentation of efficient leukocyte removal with a new filter. Transfusion, vol. 38: 64S.
10. "Bacterial Contamination of Platelets Workshop", US Department of Health and Human Services, Food and Drug Administration, Center for Biologics Evaluation and Research, 1999. Meeting notes are available online at http://www.fda.gov/cber/minutes/bact092499.pdf
    a. This website has a 300 page document that is the minutes of a meeting that was held on the topic. It is a transcript of what was said, and does not contain copies of the slides that were presented, or references.

11. Barret B B.; Anderson.; J W.; Anderson K C. 1993. Strategies for the avoidance of bacterial contamination of blood components. Transfusion, vol. March 33:3, pp. 228-233.

12. Battelle Memorial Institute, Ohio, USA, August 2000. Acute Oral Toxicity Testing of Triosyn® in Rats.

13. Beaujean F, Segier J M, Le Forestier C, Duedari N. 1992. Leukocyte depletion of red cell concentrates by filtration: influence of blood product temperature. Vox Sang, vol. 62:4, pp. 242-3.

14. Bertolini F, Porretti L, Lauri E, Rebulla P, Sirchia G. 1993. Role of lactate in platelet storage lesion. Vox Sanguinis vol. 65 pp. 194-198.

15. Bertolini, F. and Murphy, S. (1994) A multicenter evaluation of reproducibility of swirling in platelet concentrates., Transfusion vol. 34, pp. 796-801.

16. Beutler, E., 1984. Determination of 2,3-Diphosphoglycerate in Erythrocytes. Red Cell Metabolism. A Manual of Biochemical Methods. 3rd ed. Orlando, Grune & Stratton, pp. 127-129.

17. Blajchman M A. 1995. Bacterial contamination of blood products and the value pretransfusion testing. Immunol Invest, vol. January-February 24:1-2, pp. 163-170.

18. Blajchman M A.; Ali A M,; Richardson H L. 1994. Bacterial contamination of blood components. Vox Sang, vol 67 suppl 3, pp. 25-33.

19. Bove J R. 1990. Transfusion-transmitted diseases other then AIDS and hepatitis. Yale J Biol Med, vol. September-October 63:5, pp. 347-351.

20. Buchholz D H.; AuBuchon J P.; Snyder E L.; Kandler R.; Piscitelli V.; Pickard C.; Napychank P.; Edberg S. 1994. Effects of leukocyte reduction of the resistance of blood components to bacterial multiplication. Transfusion, vol 34, pp. 852-857.

21. Busch M P; Lee T. 1995. Role of Donor Leukocytes and Leukodepletion in transfusion-Associated Viral Infections. Clinical Benefits of Leukodepleted Blood Products. edited by Joseph Sweeney, M. D. and Andrew Heaton, M. D., R. G. Landes Company, chapter 8, pp. 99-112.

22. Cabantchik, Z. I., Silfen J., Firestone R. A., Krugliak M., Nissani E. and Ginsburg H., 1989. Effects of Lysosomotropic Detergents on the Human Malarial Parasite *Plasmodium Falciparum* in In Vitro Culture. Biochemical Pharmacology, vol. 38, No. 8, pp. 1271-1277.

23. Canadian Defense Research Establishement, Suffield, Canada, sponsored by Canadian Department of National Defense: Medical Coutermeasures, 1994. Biocidal Activity of Triosyn Resins.

24. Chan, K., 1997. Blood Supply: FDA Oversight and Remaining Issues of Safety. Washington, D.C., U.S. General Accounting Office 25. Chu R W. 1999. Leukocytes in Blood Transfusion: Adverse effects and their prevention. HKMJ, vol. 5, no. 3, pp. 280-284.

26. Coleman, Roger; Holdsworth, George. 1975. Effects of Detergents on Erythrocyte Membranes: Different Patterns of Solubilization of the Membrane Proteins by Dihydroxy and Trihydroxy Bile Salts. Biochemical Society Transactions, vol. 3, pp. 747-748.

27. Corash, Laurence, 1999. Inactivation of Viruses, Bacteria, Protozoa, and Leukocytes in Platelets Concentrates: Current Research Perspectives, Transfusion Medicine Reviews, vol. 13:1, pp. 18-30.

28. Dodd R Y. 1998. Transmission of Parasites by Blood Transfusion. Vox Sang, vol. 74, suppl. 2, pp. 161-163.

29. Dodd R Y. 1992. The risk of transfusion-transmitted infection. New England Journal of Medicine, vol. August 6 327:6, pp. 419-421.

30. Dodd, R Y., 1990. Will Blood Products Be Free of Infectious Agents?: Transfusion Medicine in the 1990's. In Nance S J ed. Arlington, Va., American Association of Blood Banks, pp. 223-251.

31. Fratantoni, J. C., Poindexter, B. J., and Bonner, R. F. (1984) Quantitative assessment of platelet morphology by light scattering: a potential method for the evaluation of platelets for transfusion., J. Lab. Clin. Med vol. 103, pp. 620-631.

32. G. A. Becker, M. Tuccelli, T. Kunicki, M. K. Chalos and R. H. Aster. (1973) Studies of Platelet Concentrates Stored at 22 C and 4 C., Transfusion vol. 13, pp. 61-68.

33. Geiger T.; Synder EL. 1997. Removal of anaphylatoxins C3a and C5a and chemokines IL-8 and RANTES by polyester white cell reduction and plasma filters. Transfusion, vol. 37, pp. 1156.

34. Girotti S., Ferri E., Cascione M L., Orlandini A., Farina L., Nucci S., Di Graci F., Budini R., 1991. Methodological Problems of Direct Bioluminescent ADP assay in Platelets and Erythrocytes. Anal. Biochem., February 1, vol. 192, no. 2, pp. 350-357.

35. Gómez-Abonés, X.; Pinacho, A.; Ortiz, P.; Maciá, J.; Gallart, M.; Araguás, C.; Sánchez, J. M.; Teixidó. A Simple Flow-Cytometric Method For Absolute Counting of Residual White Blood Cells in Leukocyte-Reduced Packed Red Cells. Vox Sanguinis. vol 76, pp. 64-65.

36. Greenwalt, T J and Allen, C M, 1990. A Method for Counting Leukocytes in Filtered Components. Transfusion, Vol. 30, No. 4, pp. 377-79.

37. Harmening, Denisi M., 1991. Clot Retraction, Platelet Retention/Adhesion, Platelet Aggregation, Platelet Factor 3 Availability. Clinical Hematology and Fundamentals of Hemostasis, pp. 588-592.

38. Hausser Scientific. 2002. Nageotte counting chamber recommended method for counting leukocytes in red cells products.

39. Holme S, Heaton W A. Courtright M. 1987. hnproved in vivo and in vitro viability of platelet concentrates stored for seven days in a platelet additive solution. British Journal of Haematology vol. 66:2 pp. 233-238.

40. Holme S.1992. Effect of additive solutions on platelet biochemistry. Blood Cells vol. 18:3 pp. 431-434.

41. Holme S., Moroff G., Murphy S., 1998. A multi-laboratory evaluation of in vitro platelet assays: The tests for extent of shape change and response to hypotonic shock. Transfusion, vol. 38:31, pp. 31-40.

42. Holmsen, H. (1994) Significance of testing platelet functions in vitro. Eur J Clin Invest. vol. 24, Suppl. 1, pp. 3-8.

43. Illert W E.; Sänger W.; Weise W. 1995. Bacterial contamination of single-donor blood components. Transfus Med, vol. March 5:1, pp. 57-61.

44. James G. White., (1992) Ultrastructural Changes in Stored Platelets., Blood Cells (1992) vol. 18: pp. 461-475.

45. Kekez, M M, Sattar, S A. November 1997. "A new ozone-based method for virus inactivation: preliminary study." Phys Med Biology, 42 (110), pp. 2027-39.

46. Kitasato Institute, Tokyo, Japan, sponsored by Yamada Corporation, 1994. Triosyn Air Technology Validation.

47. Klein, Harvey G.; Dzik, Sunny; Slichter, Sherrill J.; Hillyer, Christopher D.; Silberstein, Leslie E. Leukocyte-Reduced Blood Components: Current Status. American Society of Hematology.

48. Koerner K, Weihe R, Sahlmen P, Zeller B, Seifried E, Cardoso M, Kubanek B. 1995. Quality of pooled platelet concentrates prepared from buffy coats and stored in an additive solution after filtration. Annals of Hematology vol. 70:2 pp. 97-102.
49. Kubanek B.; Cardoso M.; Glück D.; Koerner K. 1993. Risk of infection transmission by blood components. Infusionsther Transfusionsmed, vol. April 20:1-2, pp. 54-59.
50. Kunicki, T. J., Tucelli, M., Becker, G. A., and Aster, R. H. (1975) A study of variables affecting the quality of platelets stored at room temperature., Transfusion vol. 15, pp. 414-421
51. Leach M F.; AuBuchon J P.; Pickard C A.; Herschel L H.; Cooper L K. Jenike D M.; Simpson S Y.; Southworth S V. 1998. Evaluation of glucose and Ph test strips in the detection of microbial contaminants in aphersis platelets. Vox Sanguinis, vol. 74(S1), p 1180.
52. Lee, Richard; Foerster, John; Lukens, John; Paraskevas, Frixos; Greer, John P.; Rodgers, George M. Wintrobe's Clinical Hematology, vol. 2, 10th ED., 1999.
53. Ledent E, Berlin G, 1996. Factors influencing white cell removal from red cell concentrates by filtration. Transfusion, vol. 36, no. 8, pp. 714-718.
54. Martin C, Boisson C, Haccoun M, Thomachot L, Mege J L, 1997. Patterns of cytokine evolution (tumor necrosis factor-alpha and interleukin-6) after septic shock, hemorrhagic shock, and severe trauma. Crit care Med, vol. 25:11, pp. 1813-19.
55. Mc Gill University Institute, Institute of Parasitology, Montreal, Canada, sponsored by Hydro Biotech, 1993. *Giardia* Cysts Challenge of Triosyn Filter.
56. Murphy S, Rebulla P, Bertolini F, et al., 1994. In vitro assessment of the quality of stored platelet concentrates. Transfus Med Rev, vol. 8, pp. 29-36.
57. New Drug Development Institute, Tokyo, Japan, sponsored by Yamada Corporation, 1996. Triosyn Intake: Oral Irritation GLP Study.
58. New Drug Development Institute, Tokyo, Japan, sponsored by Yamada Corporation, 1996. Triosyn Dermal Primary Irritation GLP Study.
59. Rebulla, Paolo and Dzik, Walter H., 1994. Multicenter Evaluation of Methods for Counting Residual White Cells in Leukocyte-Depleted Red Blood Cells. Vox Sang, Vol. 66, pp. 25-32.
60. Rosenberg R D, Aird W C, 1999. Vascular-bed-specific hemostasis and hypercoagulable states. N Engl J Med, vol. 340, pp. 1555-64.
61. Sayers M H.; Anderson K C.; Goodnough L T.; Kurtz S R.; Lane T A.; Pisciotto P.; Silberstein L E. 1992. Reducing the risk for transfusion-transmitted cytomegalovirus infection. Ann Intern Med, vol. January 1, 116:1, pp. 55-62.
62. Sazama K. 1994. Bacteria in blood for transfusion. A review. Arch Pathol Lad Med, vol. April 118:4, pp. 350-365.
63. Sherwood WC. 1993. The significance of the blood-borne viruses: blood banking and transfusion medicine. Dev Bio Stand, vol. 81, pp. 25-33.
64. Sirchia G, rebulla P, sabbioneda L, Garcea F, Greppi N, 1996. Optimal conditions for white cell reduction in red cells by filtration at the patient's bedside. Transfusion, vol. 36, no. 4, pp. 322-7.
65. Snyder E.; Mechanic S.; Baril L.; Davenport R. 1996. Removal of soluble biological response modifiers (compliment and chemokines) by a bedside leukoreduction filter. Transfusion, vol. 36, pp. 707.
66. Sweeney J D, Holme S, Stromberg R R, Heaton W A. 1995. In vitro and in vivo effects of prestorage filtration of apheresis platelets. Transfusion vol. 35:2, pp 125-130.
67. University of Montreal, Retrovirology Laboratory, Microbiology and Immunology Department, Faculty of Medicine, Montreal, Canada, sponsored by Hydro Biotech, 1997. Viral Challenge (HIV) of Triosyn Filters.
68. University of Nevada, Las Vegas, Nev., sponsored by Hydro Biotech, 2000. Effectiveness of Treated Filters in Minimizing the Concentration of Airborne MS2 in Environmental Chambers.
69. University of Rochester Medical Center. 1997. Current protocols in cytometry/editorial board, J. Paul Robinson managing editor . . . (et al.). Cell separation-Laboratory manuals.
70. U.S Department of Health and Human Services, Food and Drug Administration, Center for Biologics Evaluation and Research (CBER). May 1999. Guidance for Industry for Platelet Testing and Evaluation of Platelet Substitute Products. pp. 1-7.
71. Valeri, C. R.; Ragno, G.; MacGregor, H.; Pivacek, L. E., 1997. The Effect of Disinfection on Viability and Function of Baboon Red Blood Cells. Photochemistry and Photobiology, 65(3), pp. 446-450.
72. Valeri C. R., 1974. Oxygen Transport and Viability of Preserved Red Blood Cells. J. Med. vol. 5.
73. Valeri C R, Feingold H, Marchionni L D, 1974. The relation between response to hypotonic stress and 51-Cr recovery in vivo of preserved platelets. Transfusion, vol 14, pp. 331-337.
74. Van der Meer P F, Pietersz R N, Nelis J T, Hinloopen B, Dekker W J, Reesink H W, 1999. Six filters for the removal of white cells from red cell concentrates, evaluated at 4 degrees C. and/or at room temperature. Transfusion, vol. 39: 3: pp. 265-70.
75. Vengelen-Tyler, Virginia; Chair and Editor. Technical Manual: American Association of Blood Banks, 13th ED, Maryland, 1999.
76. Wagner S J.; Friedman L I.; Dodd R Y. 1994. Transfusion-associated bacterial sepsis. Clin Microbiol Rev, vol. July 7:3, pp. 290-302.
77. Wallas, C. H.; 1979. Sodium and Potassium Changes in Blood Bank Stored Human Erythrocytes. Transfusion, 19(2), pp. 210-215.
78. Warren H. Shaw, November 1999. Understanding Sepsis: New Findings, New Theories. Infectious Diseases Society of America, 37th Annual Meeting.
79. Weber, David J., Barbee, Susan L., Sobsey, Mark D. and Rutala, William A. 1999. The Effect of Blood on the Antiviral Activity of Sodium Hypochlorite, a Phenolic, and a Quaternary Ammonium Compound. Infection Control and Hospital Epidemiology, vol. 20, pp. 821-827.
80. Wylie BR. 1993. Transfusion transmitted infection: viral and exotic diseases. Anaesth Intensive Care, vol. February 21: 1, pp. 24-30.

What is claimed is:
1. A hemoperfusion filtration system, comprising:
a) a centrifuge for whole blood to provide a red blood cell concentrate;
b) a dilution unit for diluting said red blood cell concentrate;
c) a chamber containing a demand disinfectant iodinated resin and a plurality of diffusers for maximizing the contact of said diluted red blood cell concentrate and said iodinated resin; and
d) a pump for moving said diluted red blood cell concentrate through said chamber at a selected flow rate.
2. The hemoperfusion filtration system of claim 1, wherein said chamber is composed of a filter capsule, inlet end cap and a first mesh and a second mesh, wherein said inlet end cap is located close to said first mesh.

3. The hemoperfusion filtration system of claim 2, wherein said filter capsule comprises the plurality of diffusers present between said first mesh and said second mesh.

4. The hemoperfusion filtration system of claim 1, further comprising: c')a centrifuge for removing residual plasma that is present in said diluted red blood cell concentrate after passage through said chamber; and f') a filter for removing leukocytes.

5. The hemoperfusion filtration system of claim 1, further comprising: e''') a transfusion unit for transfusing said diluted red blood cell concentration after passage of said column into a human.

6. The system as in claim 1, wherein said centrifuge centrifuges said blood at 37° C. at 3200 RPM for five minutes.

7. The system as in claim 1, wherein said dilution unit dilutes said red blood cell concentrate using saline or other acceptable physiological fluid at 37° C.

8. A portable hemoperfusion filtration system, comprising:
 a) a means for removing plasma from whole blood to provide a red blood cell concentrate;
 b) a dilution device for diluting said red blood cell concentrate;
 c) a chamber containing a demand disinfectant, said demand disinfectant being an iodinated resin contained in said column; and
 d) a pump for moving said diluted red blood cell concentrate a blood constitute through said chamber column at a selected flow rate.

9. A hemoperfusion filtration chamber comprising a demand disinfectant iodinated resin and a plurality of hydrodynamnic diffusers, wherein the diffusers function to increase the contact efficacy between the iodinated resin and bacteria in blood that is passed through said chamber.

* * * * *

UNITED STATES PATENT AND TRADEMARK OFFICE
CERTIFICATE OF CORRECTION

PATENT NO. : 7,625,351 B2  Page 1 of 1
APPLICATION NO. : 10/938693
DATED : December 1, 2009
INVENTOR(S) : Pierre Messier It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 566 days.

Signed and Sealed this

Twenty-sixth Day of October, 2010

David J. Kappos
*Director of the United States Patent and Trademark Office*